(12) United States Patent
Cho et al.

(10) Patent No.: US 8,057,724 B2
(45) Date of Patent: Nov. 15, 2011

(54) PORTABLE WATER QUALITY SENSOR FABRICATION METHOD

(75) Inventors: Hyoung Jin Cho, Oviedo, FL (US); Shekhar Halakatti, Bangalore (IN); Anjum Mehta, Boise, ID (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 7 days.

(21) Appl. No.: 12/683,215

(22) Filed: Jan. 6, 2010

(65) Prior Publication Data
US 2010/0175821 A1 Jul. 15, 2010

Related U.S. Application Data

(60) Division of application No. 11/106,405, filed on Apr. 14, 2005, now Pat. No. 7,666,285, which is a continuation-in-part of application No. 11/044,494, filed on Jan. 27, 2005, now Pat. No. 7,569,127.

(60) Provisional application No. 60/542,564, filed on Feb. 6, 2004.

(51) Int. Cl.
*B28B 23/00* (2006.01)
(52) U.S. Cl. ............... 264/297.2; 264/645; 422/503; 204/451; 137/814
(58) Field of Classification Search .......... 204/451, 204/600, 601; 137/814, 833; 264/297.2, 264/645; 422/502–508
See application file for complete search history.

(56) References Cited

U.S. PATENT DOCUMENTS 3,465,774 A 9/1969 Kautz
4,975,175 A 12/1990 Karube
(Continued)

FOREIGN PATENT DOCUMENTS
WO WO0299410 12/2002

OTHER PUBLICATIONS

Micromolding section from Ch. 3, Fabrication Techniques for Microfluidics, Fundamentals and Applications of Microfluidics by N.-T. Nguyen & S. T. Wereley, Artech House, Boston: 2002, p. 116-117.*

(Continued)

*Primary Examiner* — Jeffrey T Barton
*Assistant Examiner* — J. Christopher Ball
(74) *Attorney, Agent, or Firm* — Brian S. Steinberger; Joyce P. Morlin; Law Offices of Brian S. Steinberger, P.A.

(57) ABSTRACT

A disposable microsensor is designed, fabricated and tested for standard BOD (Biochemical Oxygen Demand) measurements. A transparent Cyclic Olefin Copolymer (COC) substrate is used for sensor fabrication. Standard lithographic procedures in addition to techniques like screen printing and electroplating are used to fabricate the sensor. A microbial strain of *Trichosporon Cutaneum* is immobilized over one pair of sensor electrodes while the other is used as a reference. Depending on the respiratory activities of the microbial strain in different samples, the BOD values of the samples can be measured in terms of difference between the output signals. The sensor layer is attached to an injection-molded passive microfluidic channel on the top. Advantages of the BOD microsensor include, but are not limited to, fast BOD measurement, disposability because of its low cost, chemically inert polymer substrate, flow-through sample injection scheme and integration of on-chip optics.

7 Claims, 20 Drawing Sheets

U.S. PATENT DOCUMENTS

| | | | | |
|---|---|---|---|---|
| 5,085,759 | A | 2/1992 | Harker | |
| 5,409,666 | A * | 4/1995 | Nagel et al. | 422/82.07 |
| 5,536,662 | A | 7/1996 | Humphries | |
| 5,580,523 | A | 12/1996 | Bard | |
| 5,882,465 | A | 3/1999 | McReynolds | |
| 6,086,825 | A | 7/2000 | Sundberg | |
| 6,113,762 | A * | 9/2000 | Karube et al. | 204/403.06 |
| 6,251,343 | B1 | 6/2001 | Dubrow | |
| 6,287,438 | B1 | 9/2001 | Knoll | |
| 6,454,924 | B2 | 9/2002 | Jedrzejewski | |
| 6,524,790 | B1 | 2/2003 | Kopf-Sill | |
| 6,615,857 | B1 | 9/2003 | Sinha | |
| 6,645,432 | B1 | 11/2003 | Anderson | |
| 6,689,602 | B2 | 2/2004 | Keeping | |
| 6,716,620 | B2 | 4/2004 | Bashir | |
| 6,740,225 | B2 | 5/2004 | Gurry | |
| 2002/0015992 | A1 | 2/2002 | Keeping | |
| 2002/0023684 | A1 | 2/2002 | Chow | |
| 2002/0034818 | A1 | 3/2002 | Schillig | |
| 2002/0055167 | A1 | 5/2002 | Pourahmadi | |
| 2002/0093143 | A1 | 7/2002 | Tai | |
| 2002/0124896 | A1 | 9/2002 | O'Connor | |
| 2003/0023149 | A1 | 1/2003 | Montemagno | |
| 2003/0206832 | A1 | 11/2003 | Thiebaud | |
| 2003/0224506 | A1 | 12/2003 | Agrawal | |
| 2004/0053290 | A1 | 3/2004 | Terbrueggen | |
| 2004/0197899 | A1 | 10/2004 | Gomez | |
| 2005/0130292 | A1 * | 6/2005 | Ahn et al. | 435/287.1 |

OTHER PUBLICATIONS

Puntambekar, Self-Aligning Microfluidic Interconnects for Glass- and Plastic-Based Microfluidic Systems, J. Micromech. Microeng., 2002, pp. 35-40, vol. 12.

Pattekar, Novel Microfluidic Interconnectors for High Temperature and Pressure Applications, J. Micromech. Microeng., 2003, pp. 337-345, vol. 13.

Mehta, A Disposable BOD Microsensor Using a Polymer Substrate, 3rd International Conference on Sensors: Vienna Austria, 2004, p. 1-4.

Mehta, A Disposable Microbial Sensor for Rapid BOD Measurement, 8th International Conference in Miniaturised Systems for Chemistry and Life Science (micro- TAS 2004) Malmo, Sweden, 2004, p. 1-3.

Halakatti, A Disposable Microsensor for Continuous Monitoring of Fee Chlorine in Water, 2nd IEEE International Conference on Sensors, Toronto, Canada, 2003, p. 67-70.

Gartner, Polymer Based Microfluidic Devices-Examples for Fluidic Interfaces and Standardization Concepts, Proceedings of SPIE—The International Society for Optical Engineering, 2003, p. 99-104.

Mam, Microfluidic Plastic Capillaries on Silicon Substrates: A New Inexpensive Technology for Bioanalysis Chips, MEMS Conference, Nagoya, Japan, 1997, p. 1-6.

Mehta, A Disposable BOD Microsensor Using Polymer Substrates, Proceedings of IEEE, Sensors, 2004, pp. 1202-1205.

* cited by examiner (a) (b)
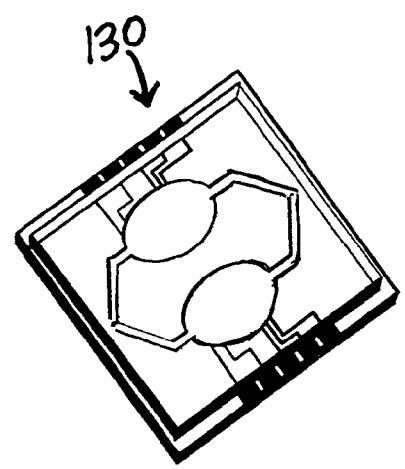 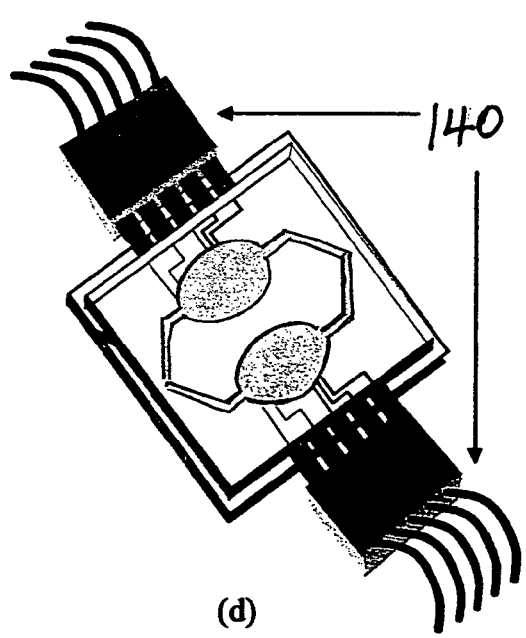
(c) (d)
Fig. 13 Fig. 14

PORTABLE WATER QUALITY SENSOR FABRICATION METHOD

This is a divisional application of U.S. patent application Ser. No. 11/106,405, filed Apr. 14, 2005, now U.S. Pat. No. 7,666,285 B1 which is a continuation-in-part of U.S. patent application Ser. No. 11/044,494, filed Jan. 27, 2005, now U.S. Pat. No. 7,569,127 that claims the benefit of priority from U.S. Provisional Application Serial No. 60/542,564 filed Feb. 06, 2004, which is hereby incorporated by reference.

FIELD OF THE INVENTION

This invention relates to microfluidic packaging and methods of use, in particular to a microfluidic package having integrated, standardized, interlocking interconnections permitting use as a package for a stand-alone microsensor or as a combination of multiple sensors and devices.

BACKGROUND AND PRIOR ART

Microfluidics is experiencing explosive growth in new product developments. Already there are many commercial applications for electro microfluidic devices such as chemical sensors, biological sensors, and drop ejectors for both printing and chemical analysis. The number of micromachined microfluidic devices is expected to increase dramatically in the near future. Manufacturing efficiency and integration of microfluidics with electronics will become important. In order to realize applications for these devices, an efficient method for packaging microfluidic devices is needed.

The biggest stumbling block to commercial success is the lack of general, simple and effective packaging techniques. Packaging of a miniaturized chemical analysis system, also known as a "lab-on-a-chip," is a very important element and plays several roles. Microfluidic packaging has to protect the sensitive functional unit from environmental factors that could affect its performance, like moisture, high temperature, vibration or corrosion. It also has to provide the component's connection to the outside world through electrical, optical and other types of interfaces. Not only should packaging not hinder function in any way, it should be a value-added asset. For example, a microfluidic sensor package would add this value if it contained a tiny pipeline to bring the media to be measured to the device reliably and efficiently. Other concepts have the package forming part of the sensing structure itself, becoming part of the device's own complex system instead of just a non-functional casing around it.

It is highly desirable that the MEMS (microelectromechanical systems) industry define a standard package for each application category. If a reasonable standard regarding inputs and outputs is available, then one microfluidic package can be appropriate for several different devices.

The present invention could serve as a standardization model for the microfluidics industry. Injection molded microfluidic packages with channels for fluid flow, input and output ports are integrally formed in the molded package. Shapes and sizes of the output ports are standardized and designed to interlock; thus, permitting the interconnection of microfluidic packages in an extended series. For packages that must pipe gases or liquids around on a chip, it will save on resources; it will mean that the entire sensor mechanism does not need to be replaced, just selected modules.

Microfluidic devices and networks in the prior art include, those containing multiple layers as reported in U.S. Pat. No. 6,645,432 to Anderson et al., and sealed by aligning two surfaces and removing a liquid to cause the seal. U.S. Pat. No. 6,615,857 to Sinha, et al. describes linearly arranged flow actuators fastened via bolts. A singular layer whereby the dispensing assembly and chip assembly engage each other with the assistance of alignment members, using vertical fluid channels in communication with pillars as shown in U.S. Pat. No. 6,454,924 to Jedrzejewski, et al. The sealing of the mated ports and reservoirs (U.S. Pat. No. 6,251,343 to Dubrow et al.) of the body structure include adhesives, bonding materials (U.S. Pat. No. 5,882,465 to McReynolds); negative pressure (US Pat. Appln. Pub. 2003/0206832 by Thiebaud, et al.); rubber O-rings (US Pat. Appln. Pub. 2002/0093143 by Tai, et al.); ultrasound welding, thermal processes (US Pat. Appln. 2002/0023684 by Chow), and the like.

Microfluidic devices with and without sensor electrode layers have been used to measure bacterial growth as described in US Pat. Appln. Publication 2004/0197899 to Gomez et al., U.S. Pat. No. 6,716,620 to Bashir et al., U.S. Pat. Appln. Publication 2003/0023149 to Montemagno et al., US Pat. Appln. Publication 2002/0055167 to Pourahmadi et al. and U.S. Pat. No. 5,536,662 to Humphries et al. Microfluidic devices have also been designed to measure chlorine as discussed in U.S. Pat. No. 6,740,225 to Gurry et al. and U.S. Pat. No. 6,689,602 to Keeping et al. U.S. Pat. No. 6,524,790 to Kopf-Sill et al. is directed to a microfluidic system that uses enzymes and software to monitor fluid flow.

Microfluidic devices for measuring biochemical oxygen demand (BOD) are discussed in U.S. Pat. Appln. Publication 2002/0034818 to Schillig et al. with a membrane reactor in the flow channel and U.S. Pat. Appln. Publication 2002/0015992 to Keeping et al. uses a membrane trap. Miniaturized oxygen electrodes are used in a microfluidic device disclosed in U.S. Pat. No. 4,975,175 to Karube et al.

The above references confirm that microfluidic devices, systems and apparatus are available; however, the problems are that the available systems are custom-made with multiple parts, limited to specific applications, expensive and in need of major improvements. C. Gartner et al. discussed one needed improvement which includes standardizing the interfacing of microfluidic devices to the macroworld in "Polymer Based Microfluidic Devices—Examples for Fluidic Interfaces and Standardization Concepts" *Proceedings of SPIE—The International Society for Optical Engineering*, Vol. 4982, pages 99-104, Jan. 27-29, 2003. C. Gartner et al. provide microfluidic devices with multiple parts that attach to standard devices, such as syringes.

There is a need for a reliable, easy to manufacture, inexpensive packaging architecture to make viable fluidic and electrical connections to micro machined microfluidic devices. The present invention provides consumers with an inexpensive, disposable, easy to fabricate, interconnecting, one-piece, microfluidic package suitable for snap-in (interlocking) configurations and for combination with integrated sensor components on a single substrate that functions as a biosensor.

SUMMARY OF THE INVENTION

The first objective of the present invention is to provide a reliable, inexpensive microfluidic package.

The second objective of the present invention is to provide a microfluidic package that affords the integration of preselected, standard sized connecting channels.

The third objective of the present invention is to provide a microfluidic package of one-piece construction that is easy to manufacture and can be batch fabricated.

The fourth objective of the present invention is to provide a microfluidic package with multiple ports.

The fifth objective of the present invention is to provide an injection molded microfluidic package with various shapes and sizes of ports that are standardized and designed to interlock.

The sixth objective of the present invention is to provide a microfluidic package capable of being interconnected in an extended series.

The seventh objective of the present invention is to provide a compact biosensor with a microfluidic layer that serves as a package and a conduit for sample solutions.

The eighth objective of the present invention is to provide a disposable Biochemical Oxygen Demand (BOD) sensor that alleviates any constraints placed on instrument portability.

The ninth objective of the present invention is to provide a disposable biosensor for applications wherein quick response time is critical.

The tenth objective of the present invention is to provide a disposable biosensor that is inexpensive and easily replaceable.

The eleventh objective of the present invention is to provide a disposable biosensor with a flow-through design that reduces contamination while allowing rapid on-line monitoring.

The twelfth objective of the present invention is to provide a disposable biosensor that can be operably connected to a portable water quality monitoring system.

A preferred multi-layer, disposable, microsensor consists of an electrode layer, a microfluidic layer with inlet/outlet ports, and an adhesive material to secure the layers in a stacked unitary arrangement. A more preferred microsensor includes a microbial layer immobilized on the electrode layer.

The preferred electrode layer has a first set of sensor electrodes, a second set of sensor electrodes and at least one temperature sensor, preferably one set of two temperature sensors.

The preferred microfluidic layer has a channel connected to a fluid reservoir that is part of a stacked unitary arrangement that permits the flow-through measurement of biochemical components in a fluid medium, such as wastewater.

A preferred disposable Biochemical Oxygen Demand (BOD) microsensor has an electrode layer, a microbial layer on the electrode layer, a microfluidic layer with inlet/outlet ports, and a means to secure the layers in a stacked unitary arrangement. The layers may be secured with adhesives or thermal bonding with the electrode layer at the bottom of the stack and the microfluidic layer at the top of the stack in the unitary arrangement.

The preferred electrode layer has a first set of sensor electrodes, a second set of sensor electrodes and one set of temperature sensors with a microbial layer immobilized on a first set of sensor electrodes.

The electrode layer and the microfluidic layer are both fabricated from a chemically inert polymer, such as, cyclic olefin copolymer (COC). The average response time for the measurement of BOD is in a range of from approximately 15 minutes to approximately one hour.

A preferred method for fabricating a disposable microsensor includes the fabrication of two layers. The first layer is the microfluidic layer fabricated by selecting a mold cavity with an inlet for injecting a chemically inert molten polymer, defining a micro pattern of microfluidic channels on a first side of the mold cavity, defining a plurality of inlet/outlet ports on a second side of the mold cavity, injecting a molten polymer into the cavity, allowing the mold to cool, allowing the molten polymer to be come a rigid substrate, removing the rigid substrate with a microfluidic channel on a first side and a plurality of inlet/outlet ports on a second side, thereby providing a one-piece, integrally formed, microfluidic package capable of permitting flow-through of a sample fluid. The second layer is an electrode layer prepared on a chemically inert, rigid polymer substrate that comprises a first set of electrodes, a second set of electrodes and one set of temperature sensors, covering the electrode layer with a dissolved oxygen selective membrane, immobilizing a microbial layer on one set of sensor electrodes, sandwiching the microbial layer between the electrode layer and the microfluidic layer, using an adhesive material to hold the electrode layer, the microbial layer and the microfluidic layer in a secure, stacked unitary arrangement.

The microfluidic channel is connected to a fluid reservoir. Both the microfluidic layer and the electrode layer are fabricated using a chemically inert molten polymer, such as, cyclic olefin copolymer. The dissolved oxygen selective membrane is silicone.

A preferred method of using a disposable microsensor includes introducing a buffering agent to a sensor device, using standard biochemical oxygen demand (BOD) solutions to calibrate the sensor, injecting a fluid sample to be analyzed for biochemical oxygen demand, using a pump and valve assembly to control the fluid flow to the sensor, controlling the fluid flow through the top microfluidic layer attached to the bottom electrode layer supporting an intermediate microbial layer, connecting the sensing circuitry in the electrode layer to a power source and a potentiostat, activating a display monitor connected to the potentiostat which reads the current flowing between a working electrode and a counter electrode in the electrode layer, and monitoring the BOD measurements in a fluid sample by reading the output data from the potentiostat as it is appears on the display monitor.

Thus, on-line measurement of biochemical oxygen demand (BOD) is accomplished when the microsensor is operably connected to a portable water quality monitoring system.

Further objects and advantages of this invention will be apparent from the following detailed description of a presently preferred embodiment that is illustrated schematically in the accompanying drawings.

BRIEF DESCRIPTION OF THE FIGURES

FIG. 1 shows details of the structure of the interconnecting and interlocking microfluidic package.

FIG. 3 shows how the microfluidic package of the present invention can be adapted for use as a dielectrophoretic manipulation chip.

FIG. 6 shows the use of injection molding method for making a one-piece microfluidic package using mold insert and blocks.

FIG. 8 is an example of fabricated microfluidic packages.

FIG. 13 is the completely assembled sensor layer and fluidic layer.

FIG. 14 is a sensor chip with electrical connections.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

The terms "microsensor" and "biosensor" are used interchangeably herein to refer to a sensor that is extremely small in size that detects information about a specific variable such as temperature, light, glucose concentration, oxygen consumption or any substance undergoing analysis or being measured.

The microfluidic package of the present invention has two or multiple integrated interconnections with a pre-selected, standard size or various other sizes with one size fitting into the other. The fluidic interconnector in one component snaps in the fluidic interconnector in another component resulting in interlocking action between the components. This allows the microfluidic devices to be connected in series without resorting to extra tubing connections or bonding processes. The design of the microfluidic package also permits reconfiguration of a series of connections.

The combination of multiple sensors and devices is facilitated. Furthermore, the one-piece construction of the microfluidic packaging eliminates complicated alignment processes for attachments as reported in the prior art. In the present invention, microfluidic channels and containers and other fluidic components are fabricated on the flat side of the package simultaneously or afterwards via injection molding, embossing, casting or various other means. The fabrication method using injection molding guarantees replication of the microfluidic patterns from micro machined molds on one side while generating interconnections on the other side. This saves time and cost involved in post-processing of interconnections in various microfluidic devices.

Figure 1A:
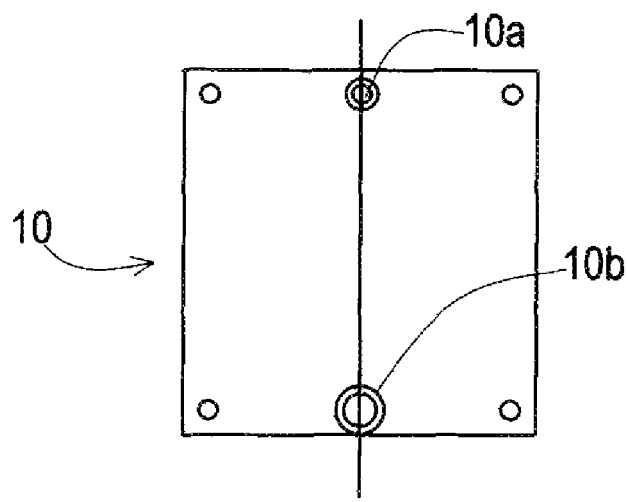
FIG. 1A shows a first side of the microfluidic package with strategic locations of interconnecting inlet/outlet ports.
Figure 1B:
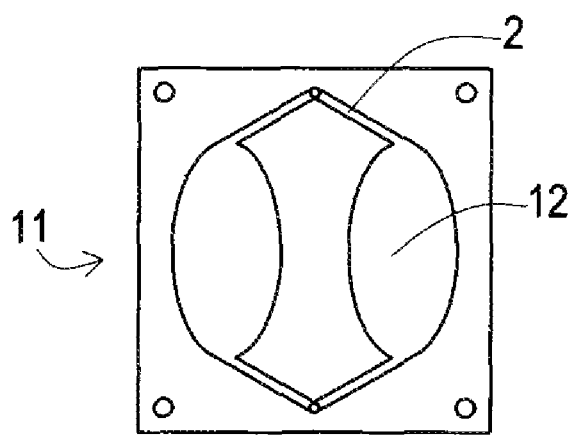
FIG. 1B shows a second side of the microfluidic package with connecting channels and fluid reservoirs or chambers.
Figure 1C:
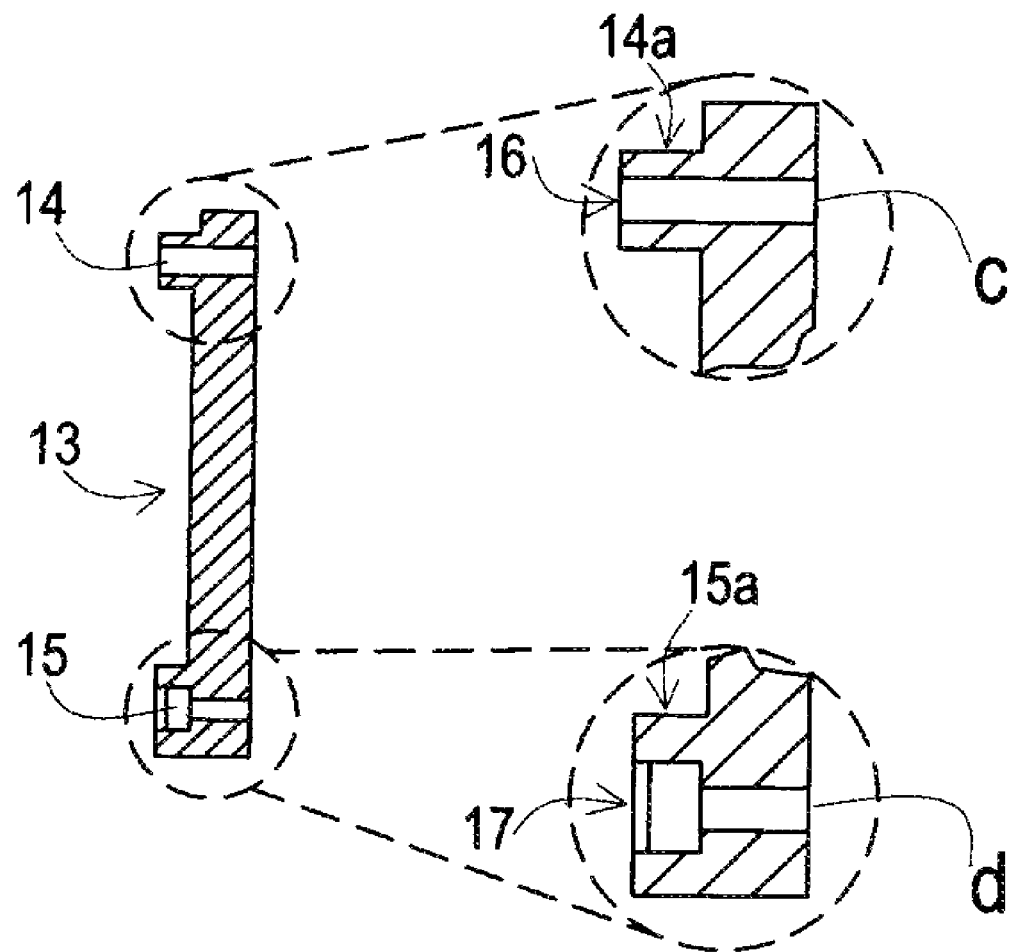
FIG. 1C shows the detail and design of male-female interlocking ports enlarged on a scale of 8:1.

FIG. 1 shows structural details of the microfluidic package or device of the present invention. FIG. 1A is a plan view 10 of a first side of a microfluidic package with interconnecting ports 10a and 10b. The smaller port 10a is designed to friction-fit snugly into the larger port 10b, when two microfluidic packages are interconnected. FIG. 1B shows a second side 11 of the microfluidic structure with areas defined as microfluidic channels 2 and fluid reservoirs or chambers 12. In FIG. 1C, a side view 13 of the microfluidic package is shown with interlocking ports 14 and 15. Greater detail and design of each port is enlarged on a scale of 8:1. The smaller port 14a and the larger port 15a have inlet tubes c and d, respectively, wherein the diameter of the tube is approximately 0.50 millimeters (mm). Both ports 14a and 15a have outlet tubes 16 and 17, respectively, with standard tubing diameters such as, approximately $\frac{1}{16}$ inch, approximately $\frac{1}{32}$ inch and approximately $\frac{1}{64}$ inch. The outer diameter of the smaller male port 14a fits into the larger female port 15a. Standardized sizes for outlet tubes 16 and 17 combined with the male-female interlocking function of the ports make this package versatile for use as a common platform between different components. The present invention is suitable for applications using pre-selected, standard size outlet tubes in the United States (US) and non-US countries. The outlet tubes can also be used in a variety of applications.

Figure 2A:
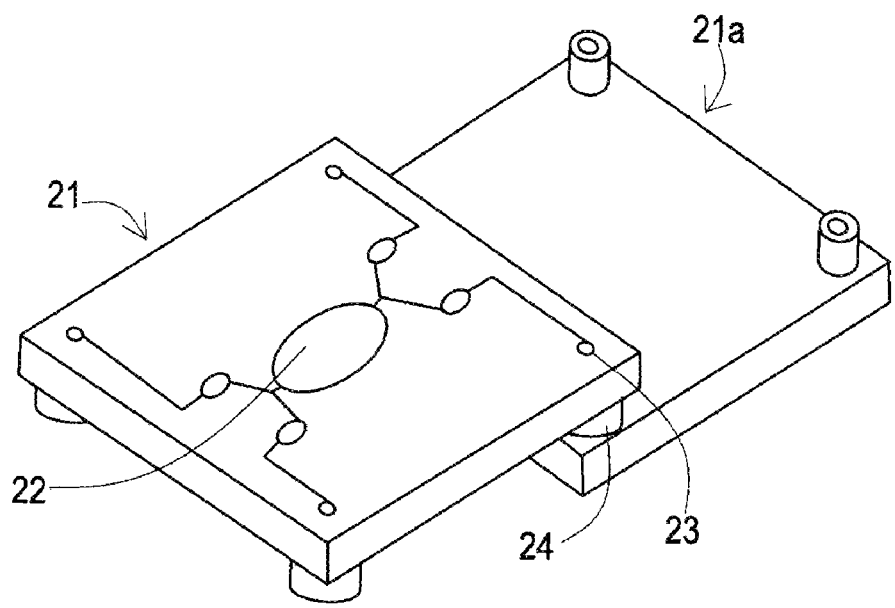
FIG. 2A shows a perspective view of two four-port microfluidic packages interconnected.

FIG. 2A illustrates the interlocking function of a microfluidic package, in which two ports in one component 21 are mating with two ports from another component 21a. A first side of the microfluidic package 21 shows the microfluidic channel and reservoir structure 22. The microfluidic structure is connected to an input port 23 and an output port 24. Fluid flows are injected through the ports, accommodated by the channels and reservoirs in the microfluidic structure and continue in channels and connections to different devices.

Figure 2B:
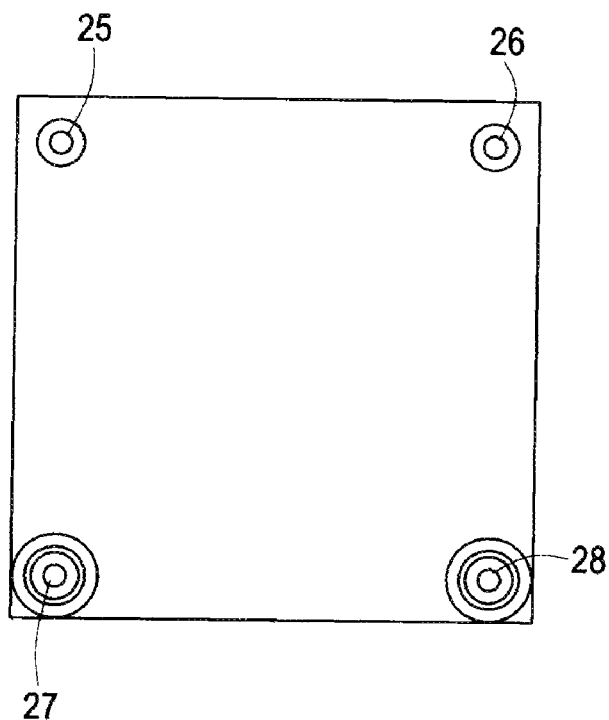
FIG. 2B shows a plan view of a first side of a four-port microfluidic package.

FIG. 2B is a plan view of the embodiment of the present invention, where a four-port design is employed. The smaller male ports 25 and 26 are designed and sized to connect and interlock with the larger female ports 27 and 28 of a different chip or microfluidic package fabricated by the process of the present invention.

FIG. 3 illustrates how the design of the present invention can be adapted for use as a dielectrophoretic manipulation chip. In FIG. 3A, a plan view 30 of a microfluidic package is shown with a microfluidic channel 32 fabricated on the bottom surface. A smaller port 31 and a larger port 33 are at opposite ends of the microfluidic channel 32 and are connected to channel 32 by fluid channels 3 and 6. FIG. 3B shows a cross-sectional view of inlet/outlet port 31a, the microfluidic channel 32a and inlet/outlet port 33a. The smaller male port 31a is sized to fit snugly and interlockingly, without the use of adhesives or bonding agents, into the larger female port 33a of an interconnecting microfluidic package.

Figure 3A:
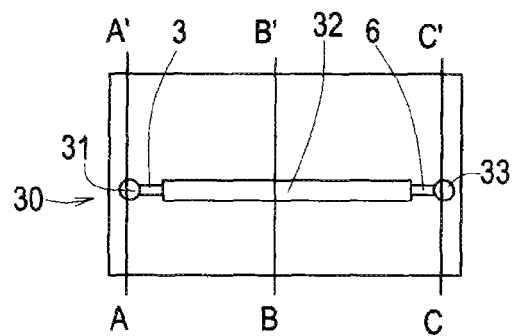
FIG. 3A is a plan view of a microfluidic package showing a male port, a microfluidic channel and a female port.
Figure 3B:
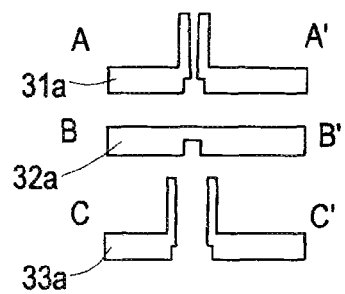
FIG. 3B shows cross-sectional views of a male port along line A, A', a microfluidic channel along line B, B' and a female port along line C, C' of FIG. 3A.
Figure 3C:
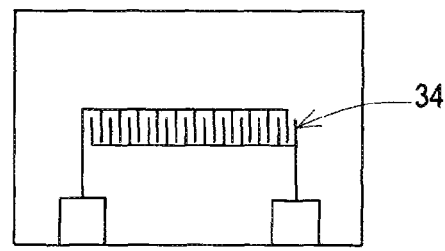
FIG. 3C is an interdigitated array type electrode for dielectrophoretic manipulation.
Figure 3D:
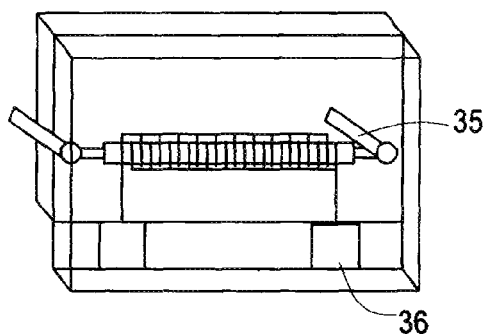
FIG. 3D shows placement of a microfluidic package over the electrode of FIG. 3C to complete the dielectrophoretic cell separation chip.

FIG. 3C is an example of an interdigitated array type electrode 34 on a substrate for dielectrophoretic manipulation. It is understood that the electrode type can vary according to the design chosen by someone skilled in the art and is not a limitation on the present invention. Further, as an example, FIG. 3D shows a fluidic inlet/outlet 35 on the microfluidic package over the electrode and an electrical connection 36 completes the dielectrophoretic cell separation chip.

Figure 4:
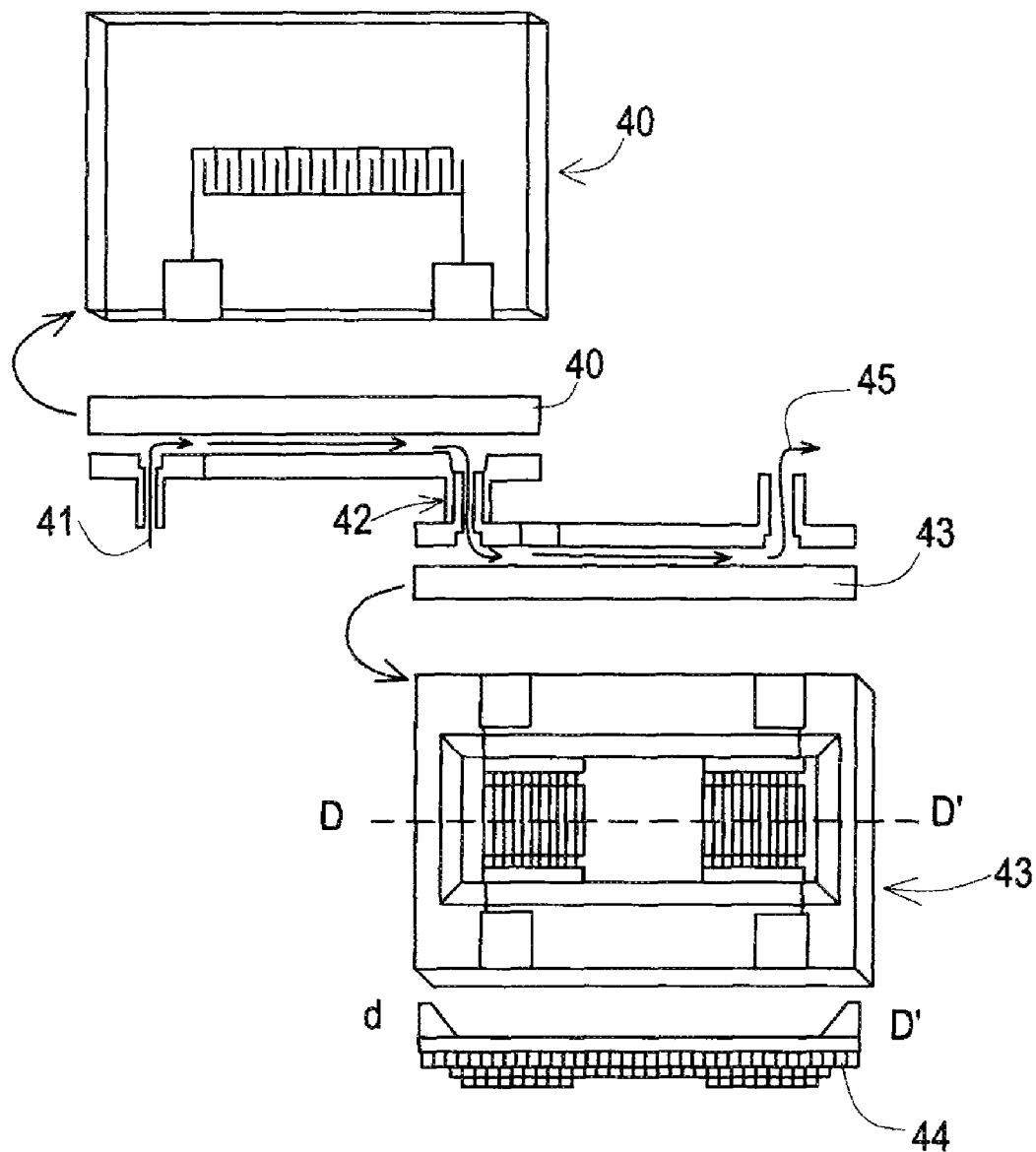
FIG. 4 is a cross-sectional view of serial connections of multiple components using interconnected microfluidic packages.

FIG. 4 illustrates the serial connection of multiple components with the present invention. Various types of devices and components can share the microfluidic package platform of the present invention and can be configured to have a new synergetic function; the type of device and component is not a limitation of the present invention. In FIG. 4, an interdigitated array type electrode on a substrate for dielectrophoretic manipulation 40 receives a fluidic sample injection through an inlet port 41; the fluid flows through interconnected and interlocked port 42, across a biosensor chip 43 and finally through outlet port 45. The arrangement of microfluidic packages in FIG. 4 includes a plan view of a dielectrophoretic manipulator chip 40, a cross-sectional view of connecting and interlocking inlet/outlet ports 41, 42, and 45, a plan view of the biosensor chip 43 and a cross-sectional view 44 of a the biosensor chip 43 along the line D, D'.

Referring now to fabrication methods for the novel microfluidic package of the present invention, the packaging can be mass-produced with inexpensive polymer materials. The classes of materials that can be used to fabricate the microfluidic package include, but are not limited to, acrylics, olefins, polycarbonates, polyesters, polyethylene, polypropylene, polystyrene, polyurethane, poly vinyl compounds, fluorocarbons, epoxies, silicones and other materials useful in injection molding, casting or embossing. Thus, someone skilled in the art can select from a wide variety of materials that are compatible with fluids, devices and testing environment.

Figure 5:
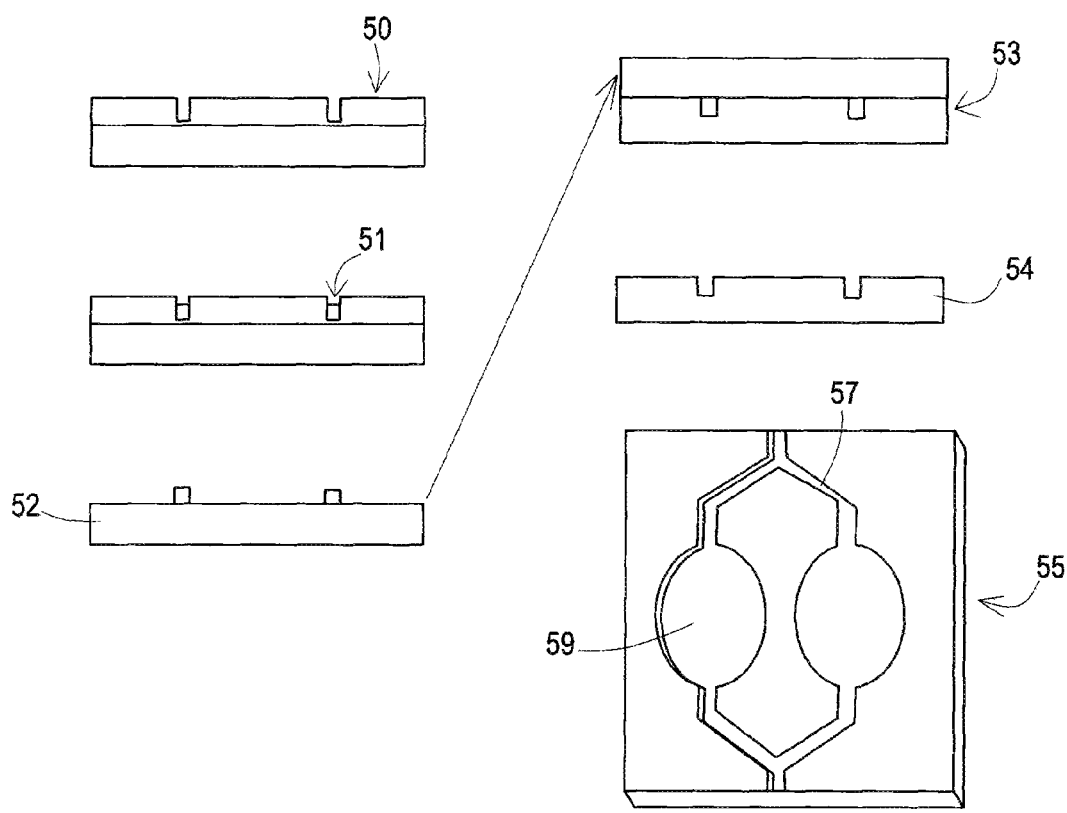
FIG. 5 shows one method of fabricating a microfluidic structure for a one-piece microfluidic package using electroplating followed by microinjection molding or microembossing.

FIG. 5 shows a fabrication method for a microfluidic structure with channels and reservoirs created in one side of a microfluidic package. Photolithography defines micro patterns on a first side, such as, a metal or metallic substrate 50 and electroplating is performed over the open area 51. A photo resist strip 52 is removed and a mold insert is made. The mold insert is used to replicate a pattern on the polymer material 53. It is also possible to use injection molding, casting or embossing to replicate a pattern onto a polymer material. A side view 54 and a plan view 55 of the completed microfluidic structure show channels 57 and reservoirs for fluids 59.

Figure 6A:
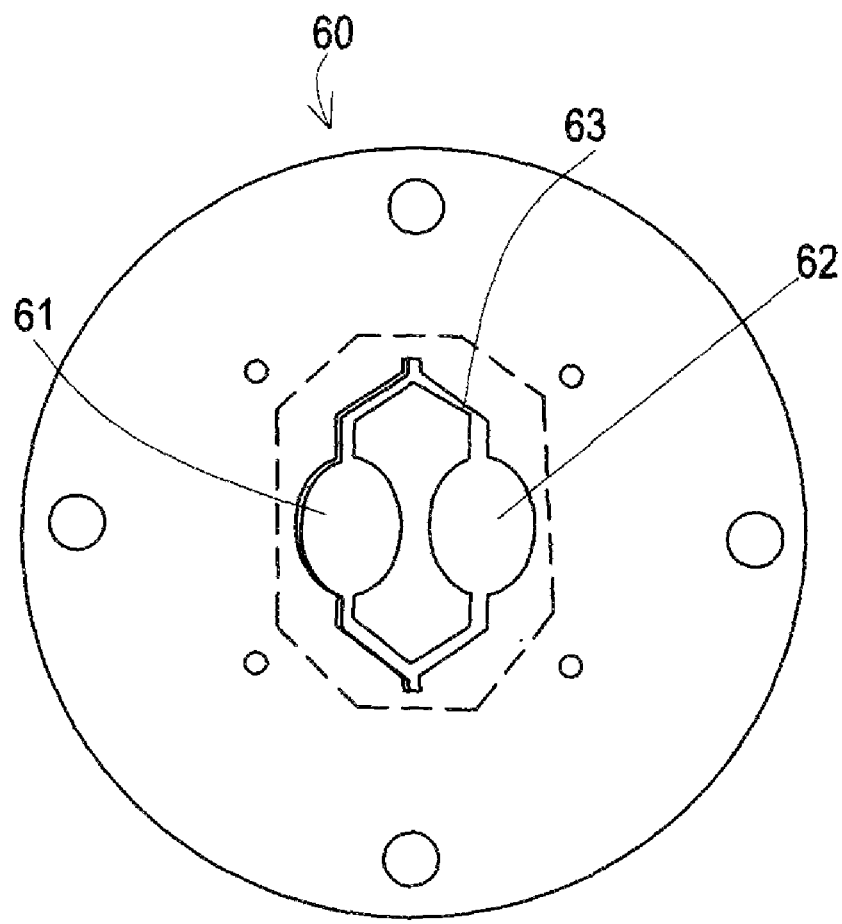
FIG. 6A is a plan view of a mold insert with fluid reservoirs connected to fluid channels.
Figure 6B:
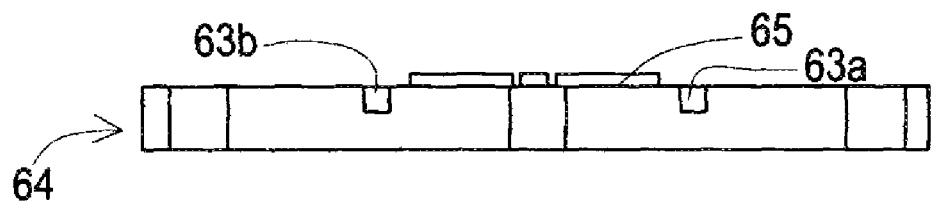
FIG. 6B is a cross-sectional view of the mold insert of FIG. 6A.
Figure 6C:
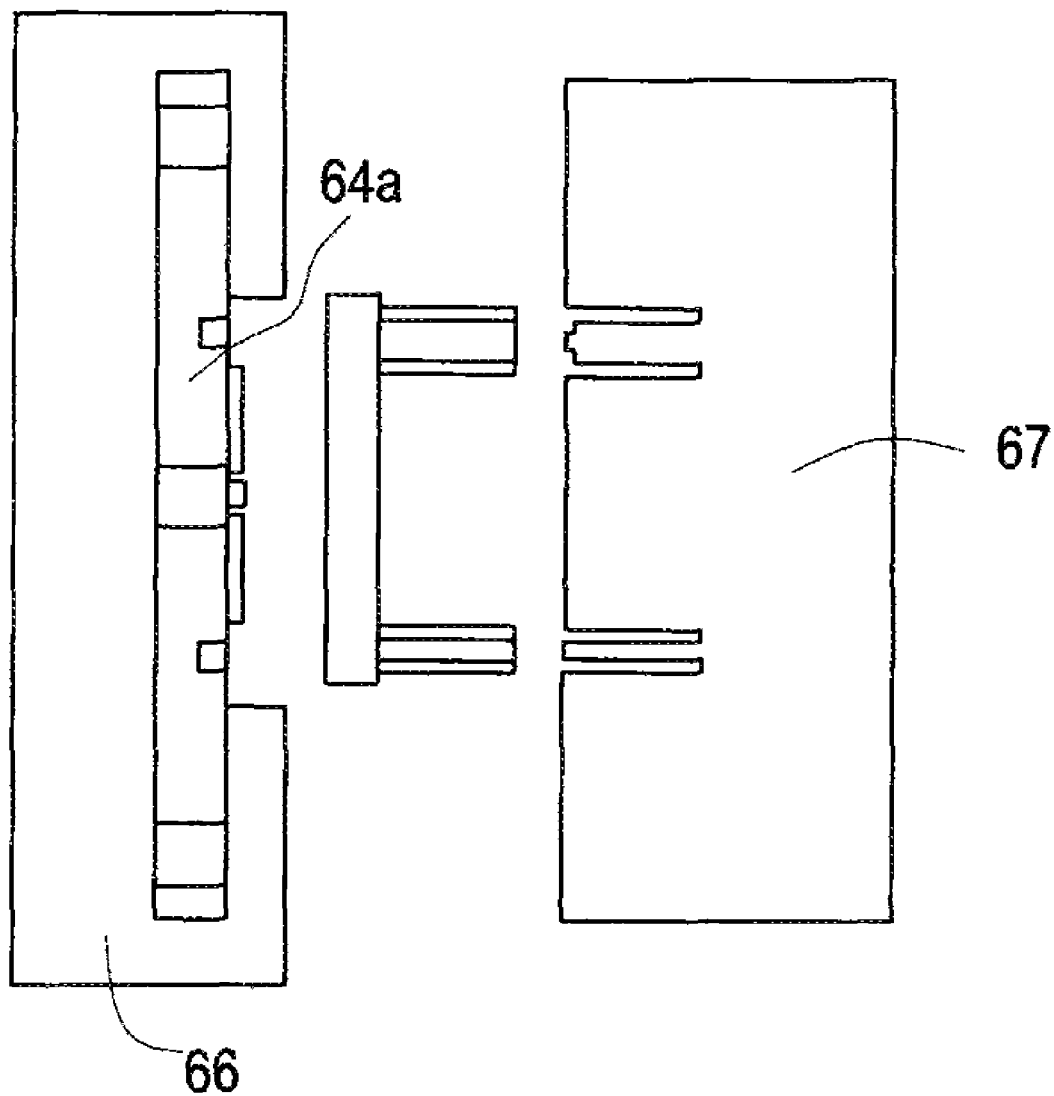
FIG. 6C is an exploded view of the mold insert and the alignment of the insert in the mold block.

FIG. 6 shows a fabrication method of the microfluidic package using mold blocks. In FIG. 6A, a plan view 60 of the mold insert that shows fluid reservoirs 61 and 62 connected to fluid channels 63. FIG. 6B is a cross-sectional view 64 of the mold insert and shows the location of fluid channels 63a and 63b and the raised surface 65 that is used to form the fluid reservoirs. In FIG. 6C, the fabricated mold insert 64a is clamped inside the mold form 66 and aligned with a mold block 67. Inlet and outlet ports in a second substrate 68 are defined by mold block 67, while the microfluidic structure is defined by mold insert 64 inside of mold block 66. The fabrication of mold block 67 is by a well-known method of EDM (electro-discharge machining) or the same technique illustrated in FIG. 5 can be used.

Figure 7:
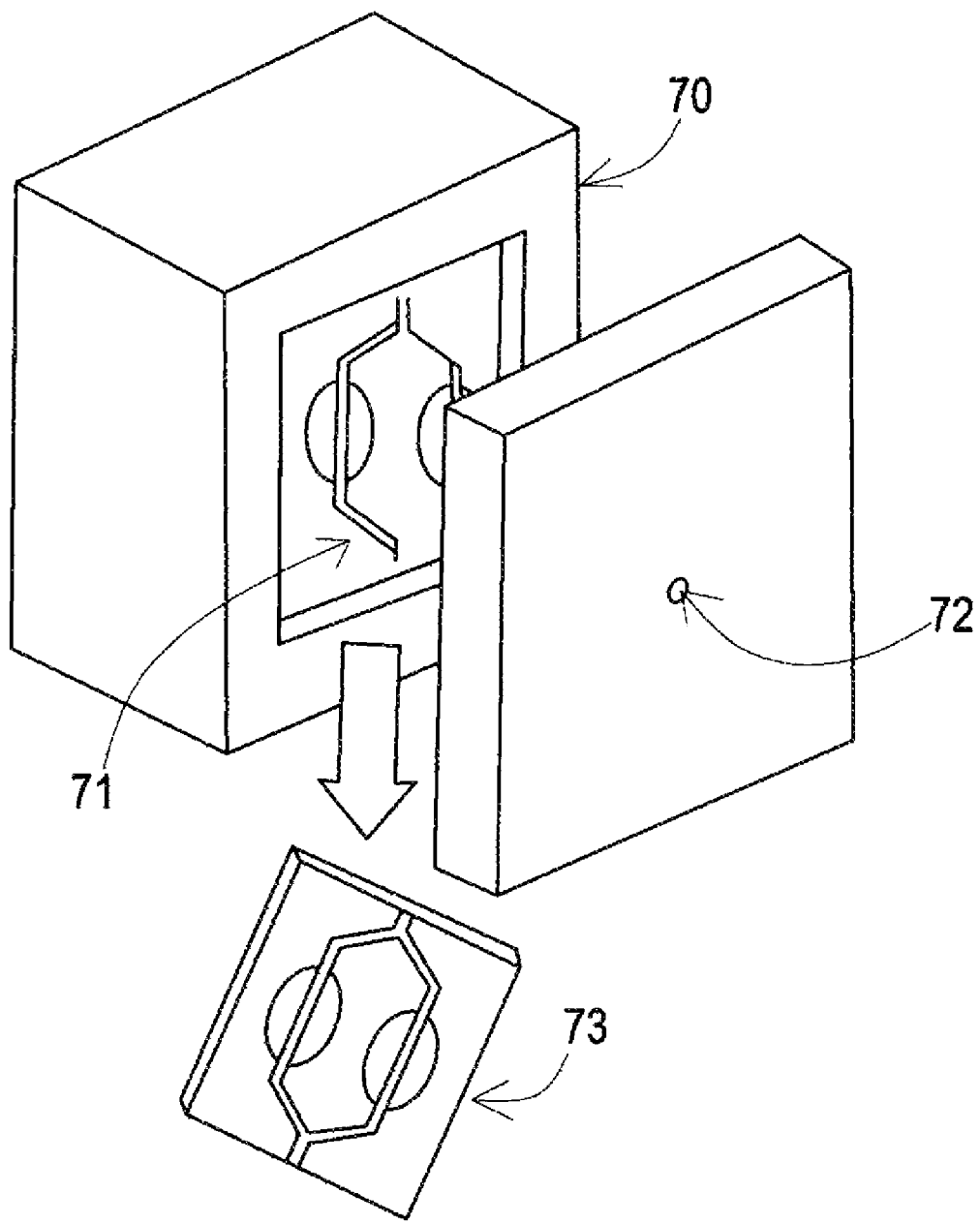
FIG. 7 shows the injection molding method of fabricating the one-piece microfluidic package.

A preferred method of fabricating the microfluidic package of the present invention is illustrated in FIG. 7, which is a perspective view of the injection molding process. Injection molding is a well-known process. A clamping block or mold 70 holds a mold insert 71. A molten, fluid polymer or polymer-based resin is inserted through nozzle 72 and is then allowed to cool and harden to replicate the pattern of 71, thereby forming a one-piece microfluidic package 73 having microfluidic channels with or without fluid reservoirs on a first substrate and inlet and outlet ports on a second substrate that engage by male-female friction fit.

Figure 8A:
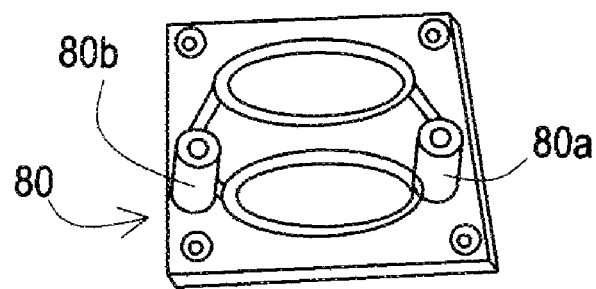
FIG. 8A is a single microfluidic package.
Figure 8B:
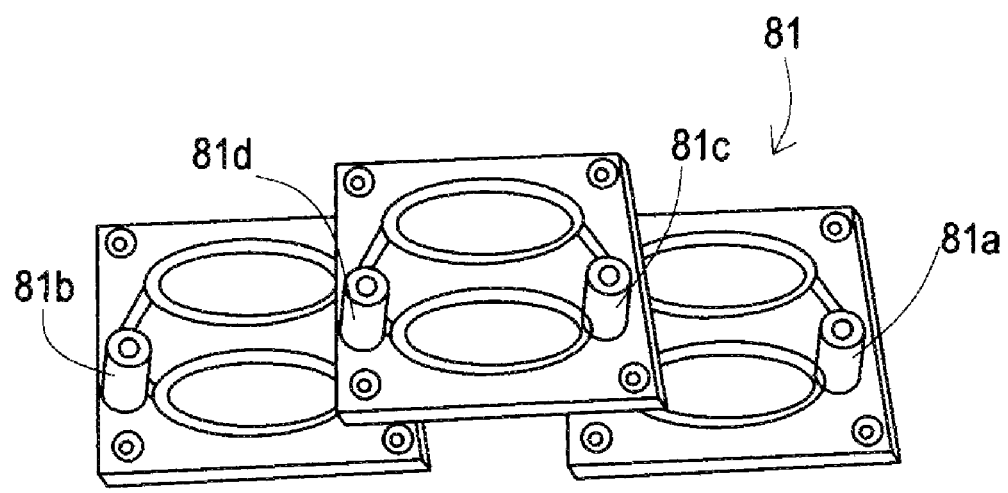
FIG. 8B is a series of three microfluidic packages in an interconnected horizontal arrangement.

FIG. 8 shows the microfluidic package of the present invention as an individual package and also as connected in a series. In FIG. 8A, a single package 80 includes a microfluidic structure with inlet/outlet ports 80a and 80b in a two-port design. Interconnected packages 81 are shown in a series where inlet/outlet ports 81a and 81b are at the peripheral ends of the series. Interconnecting ports 81c and 81d are used to join three individual microfluidic packages in one connected series. It is understood by persons skilled in the art that the interconnecting microfluidic structures could have multiple connections and configurations that extend in vertical and horizontal directions as long as there are available inlet/outlet ports that engage by male-female friction fit.

There are many value-added features of the novel microfluidic package disclosed herein, including, but not limited to, ease of manufacture, and increased utilization of known materials, versatility, reliability, accuracy and economy. The present invention resolves problems in fluidic interconnection by providing standardized, integrated inter-connections that easily combine and reconfigure devices using interlocking action. Thus, a common packaging platform is now available to form a flexible array of devices and components, which include, but are not limited to, a bio/biochemical/chemical sensor chip, a dielectrophoretic manipulator chip, and a microfluidic reactor chip.

Two examples of the use of the microfluidic device of the present invention are provided below. The first example is a disposable microsensor for continuous monitoring of free chlorine in water. The second example is a disposable microbial sensor for rapid BOD measurement. These examples do not require the interlocking, interconnecting feature, but take advantage of one-piece polymeric construction of the microfluidic device 80 shown in FIG. 8A with inlet/outlet ports 80a and 80b. Thus, the packaging of a microfluidic structure or device with a microelectrode results in a unique sensor with fast response time.

Polymeric material is used for sensor fabrication as well as the material to create the microfluidic layer. More specifically, a transparent cyclic olefin copolymer (COC) is preferred for its durability, chemical-inertness, and low cost.

With regard to the development of a disposable microsensor for monitoring free chlorine in water, the following background information is provided to emphasize the need for improved devices. Chlorination is a cheap and reliable water treatment technique. In the United States, water borne disease has been controlled primarily by chlorination, which is an essential part of typical drinking water treatment processes to prevent bacterial proliferation in the water distribution systems. The use of chlorine, however, requires caution since it also reacts with organics and forms disinfection by-products, such as carcinogenic chloroform. High chlorination will also result in corrosion of water distribution systems and adds odor to water. Thus, to ensure the safety of public health, it is very important to accurately and effectively monitor chlorine residuals during the treatment and transport of drinking water. Standard methods for measuring free chlorine are not generally portable and require expensive instrumentation or have limitations in lifetime and on-line measurement.

EXAMPLE 1

Chlorine Sensor

Figure 9:
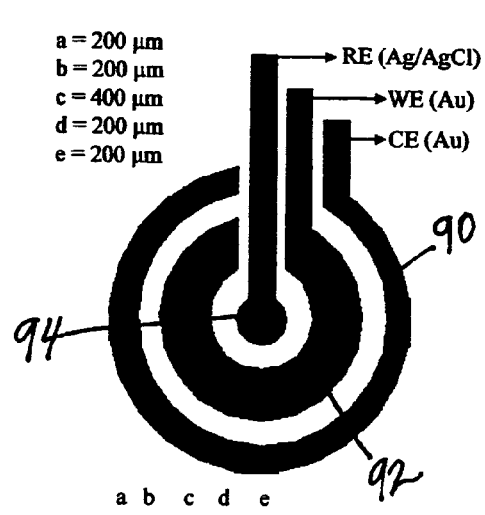
FIG. 9 shows the sensor electrode structure with dimensions.

Sensor Design—Using a cost-effective rugged cyclic olefin copolymer (COC) substrate, two layers are designed; a sensor electrode layer and a fluidic layer. For a chlorine sensor, gold (Au), gold (Au) and silver/silver chloride (Ag/AgCl) comprise working, counter and reference electrodes respectively. For a temperature sensor, a meander-type gold (Au) resistor of 1 square millimeter ($mm^2$) was designed. The temperature sensor was included to monitor the sample water temperature and to take into account any thermal effect on the chlorine concentration. The electrode structure and dimensions are shown in FIG. 9. A concentric three electrode design is shown wherein; the outermost curved electrode is the counter electrode (CE) 90 made of a strip of gold (Au) 200 micrometers (μm) in width. The curved working electrode (WE) 92 is spaced 200 μm inside the counter electrode (CE) 90 and is made of a strip of gold (Au) 400 μm in width. The reference electrode (RE) 94 made of a silver/silver chloride (Ag/AgCl) strip, is spaced 200 μm inside the working electrode (WE) 92, is 200 μm in diameter, and forms a bulls-eye in the center of the outer rings formed by the working electrode (WE) 92 and counter electrode (CE) 90 both made of gold (Au).

Figure 10:
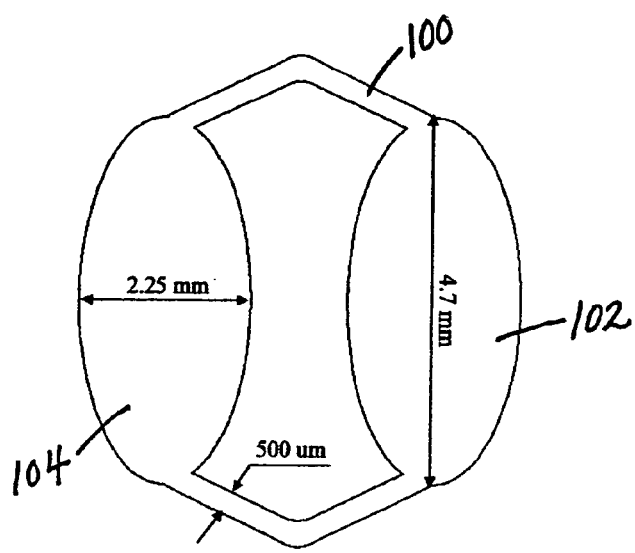
FIG. 10 shows the one-piece microfluidic channel and reservoirs with dimensions.

FIG. 10 shows the configuration of the fluidic layer with microchannels 100 that are 500 micrometers (μm) in diameter connecting fluid reservoirs 102 and 104; each reservoir has a cavity that is approximately 2.25 millimeters (mm) wide and approximately 4.7 mm in length.

Figure 11:
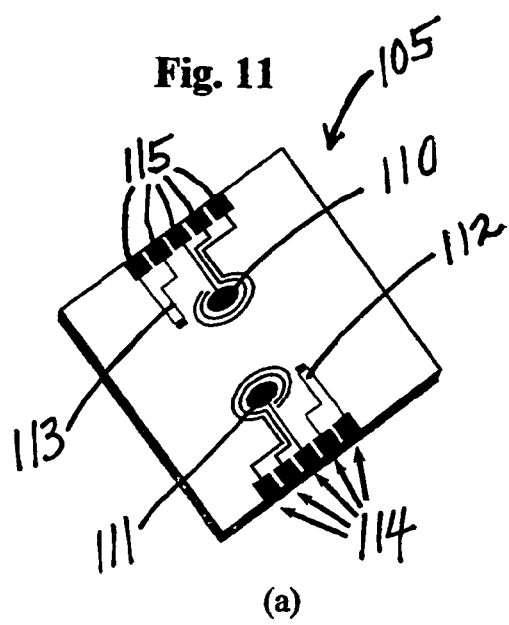
FIG. 11 is the sensor electrode layer with chlorine sensors, temperature sensors and electrodes.
Figure 12:
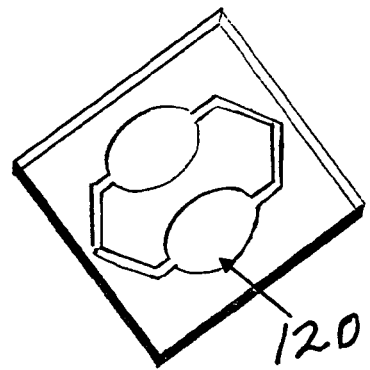
FIG. 12 is the microfluidic channel layer.

Design and operation of the sensor are schematically illustrated in FIGS. 11-14. FIG. 11 shows the sensor electrode layer where 110 and 111 are the chlorine sensors, 112, 113 are the temperature sensors and 114, 115 are the electrodes. FIG. 12 shows the one-piece microfluidic channel and reservoirs 120 fabricated as disclosed herein. FIG. 13 shows the assembled sensor layer and fluidic layer 130 adhesively aligned and secured to form the completed sensor. FIG. 14 shows the sensor chip with electrical connectors 140 for the operation of the disposable electrochemical microsensor.

Sensor Fabrication

Figure 15:
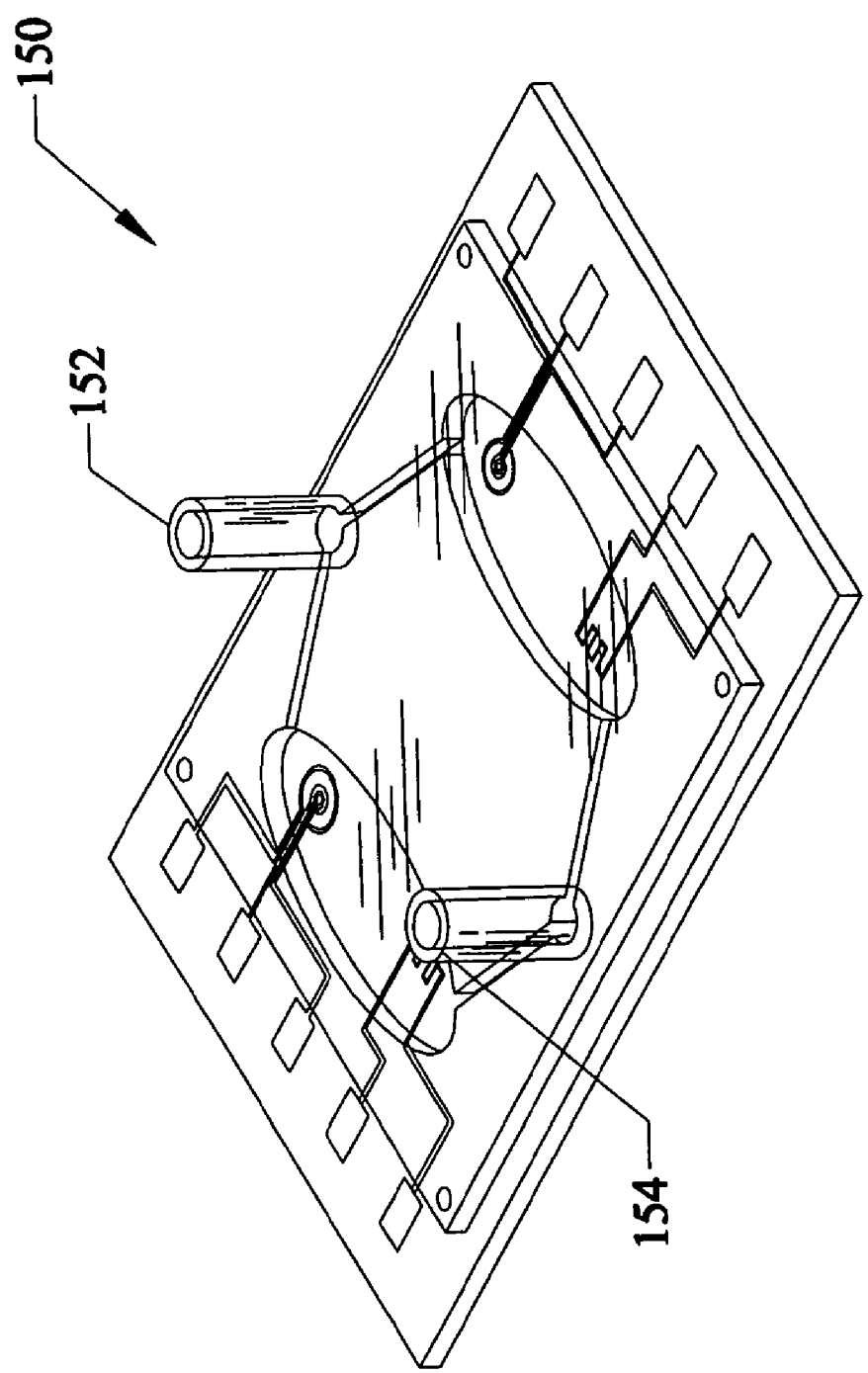
FIG. 15 is an assembled view of the flow-through chlorine sensor.

A 3" cyclic olefin copolymer (COC) wafer coated with gold (Au) by electron beam evaporation was used as the substrate. The electrode was patterned on the substrate using photolithography. In the regions where the photoresist was opened, silver (Ag) was electroplated onto the gold surface. The silver surface was then chlorinated in 0.1M KCl to form the Ag/AgCl reference electrode. The photoresist was used as a protective layer for gold etching and to cover the gold lines and unwanted regions from unnecessary exposure to the analytes. The temperature sensor was fabricated by gold (Au) etching. The coated and etched COC substrate was then cut into individual devices. The completely fabricated sensor electrode along with the temperature sensor is shown in FIG. 11. The fluidic layer 120 shown in FIG. 12 is assembled with the sensor electrode layer using adhesive to form an assembled flow-through chlorine sensor 150 as shown in FIG. 15 with inlet/outlet ports 152 and 154.

Testing and Results

Free residual chlorine sample solutions were prepared by varying the dilution of a 63.65 ppm standard chlorine solution (Hach Company USA) and adjusting the pH of the prepared samples by adding an appropriate amount (few drops) of 0.1N NaOH. Free chlorine is the sum of hypochlorous acid (HOCl) and hypochlorite ions ($OCl^-$). The ratio HOCl to $OCL^-$ is pH and temperature dependent. When the pH increases, the fraction of hypochlorous acid decreases and the fraction of hypochlorite ions increases. Since the sensor responds to $OCL^-$ ions alone, the operating pH was kept at 9. The resulting free chlorine concentrations were in parts per million (ppm). Free chlorine concentrations for each sample were measured using HACH DR/4000 spectrophotometer (Hach Company, U.S.A). To ensure the accuracy of the Hach measurements, DPD (N, N-diethy-p-phenylenediamine) ferrous titrimetric method was also performed. Sample water flow was introduced and controlled by a syringe pump (NE 1000, New Era Pump systems). Electrochemical measurements were made by connecting the sensor to a Multistat potentiostat from Sycopel.

Figure 16:
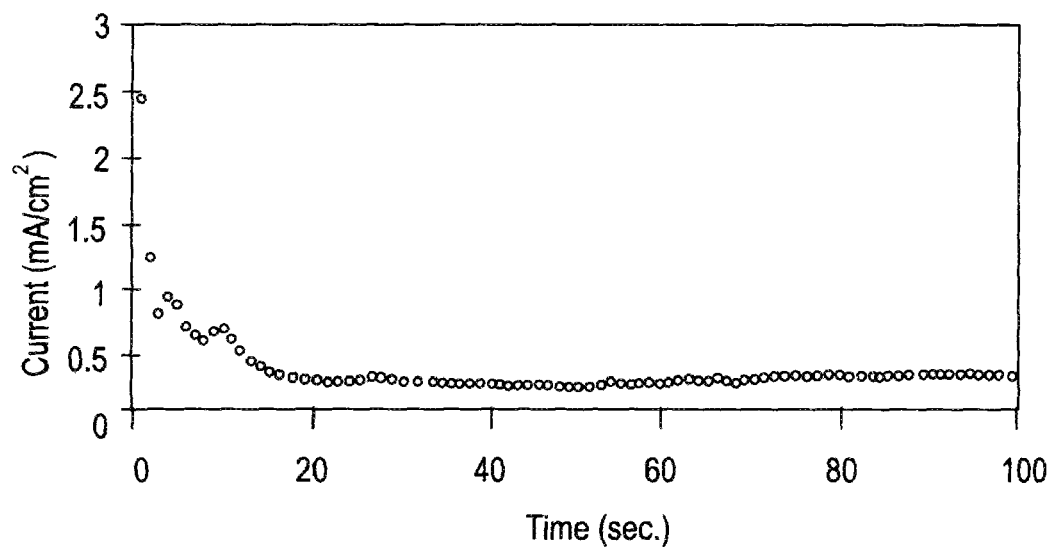
FIG. 16 is a graph of the time variation of sensor output measured in a solution with 4.0 ppm chlorine.
Figure 17:
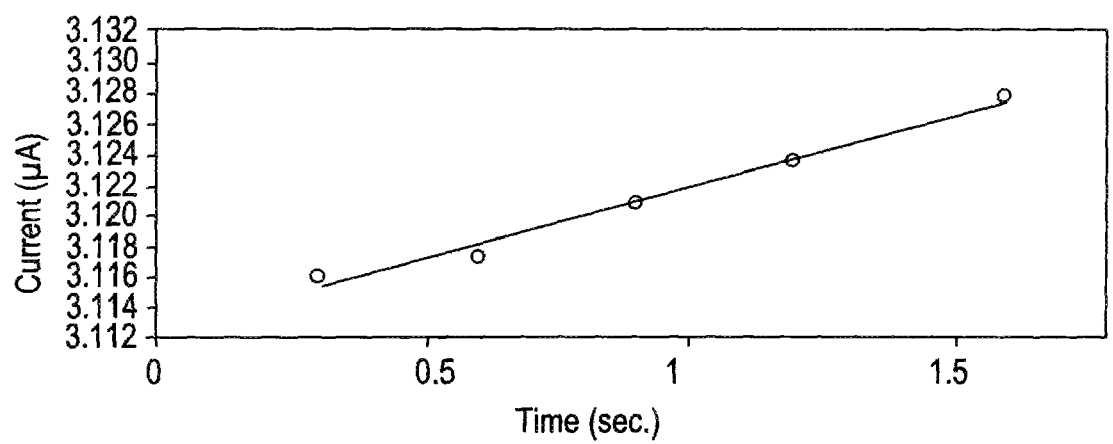
FIG. 17 is a plot of sensor output as a function of free chlorine concentration.

After the reduction potential of free chlorine was established by cyclic polarization using known techniques, potentiostatic polarization experiments were performed on the various samples. FIG. 16 shows an example potentiostatic polarization on a sample with 4 ppm $OCl^-$ ions. The figure shows that an initial settling time of about 20 seconds was required before stable output was observed. Since the electrochemical sensor follows the principle of amperometry the observed current is a function of the analyte (in this case $OCl^-$ ions). Potentiostatic polarization is performed for all samples. The stable current output from all the potentiostatic polarization experiments were tabulated and plotted against the sample concentration as shown in FIG. 17. The sensor shows a good linear response in the range of approximately 0.3 ppm to approximately 1.6 ppm.

Temperature Sensor

Figure 18:
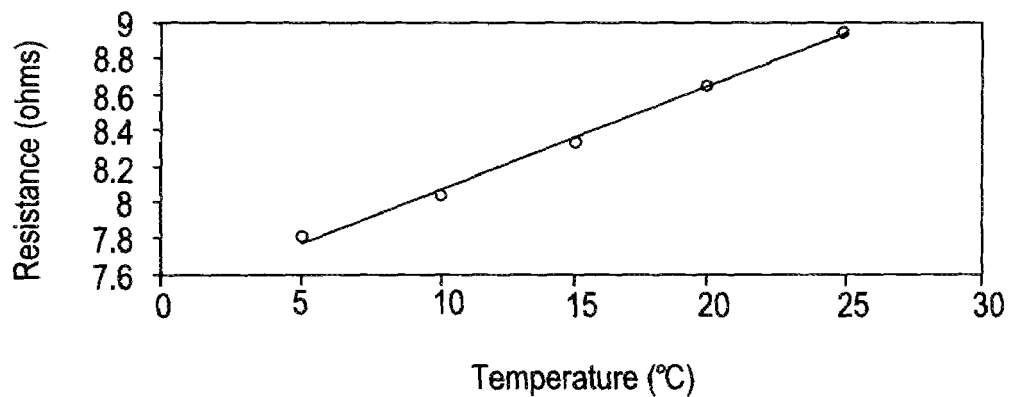
FIG. 18 is a plot of the variation of resistance of the temperature sensor with respect to temperature.

The change in resistance with increase in temperature of the sample was plotted and is shown in FIG. 18. It is observed that the change is linear in the range of approximately 5° C. to approximately 25° C. Once the resistance is calibrated the temperature of the sample can be directly read.

Flow-Through Measurement

Figure 19:
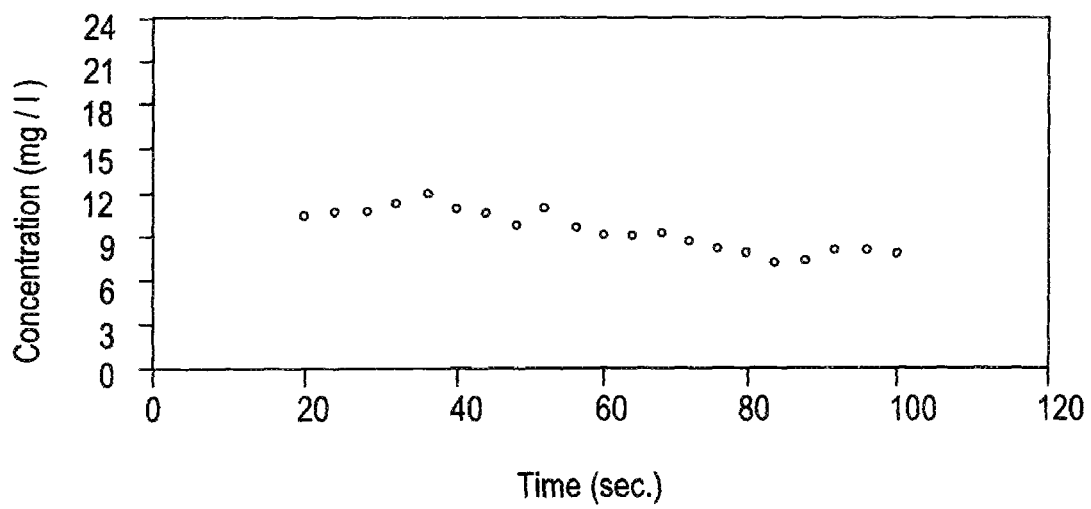
FIG. 19 is a plot of time variation of concentration during flow-through measurement of a sample with 8 ppm free chlorine.
Figure 20:
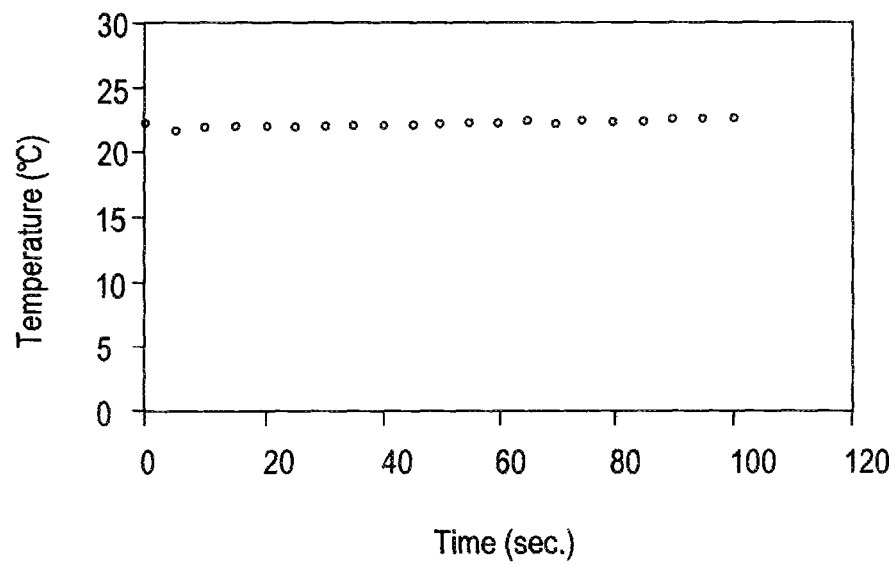
FIG. 20 is a plot of the variation of temperature inside the sensor cell during the flow-through measurement.

FIG. 19 shows the results of time variation of the sensor output. A chlorine concentration of 8 ppm at pH 9 was chosen. Although trapped air affected sensor performance, fairly stable signal output was observed under flow-through rate of 5 ml/min. The temperature was also measured simultaneously to account for any change in concentration with respect to temperature. FIG. 20 shows the operating temperature variation measured during the sensor operation. This demonstrates the stability of the sensor at this flow rate.

Example 1 describes the fabrication, design and operation of a disposable microsensor for continuous monitoring of free chlorine in water. The sensor is tested using water samples with a known quantity of free chlorine. The sensor showed a linear response to the variation in free chlorine concentration varied between approximately 0.3 ppm to approximately 1.6 ppm at pH 9. Flow-through measurement was conducted and showed satisfactory results for an on-line, continuous monitoring device.

Prior to describing the BOD Sensor of the present invention, a brief explanation of the current technology for BOD measurements is provided. The present invention provides for flow-through measurement in enclosed microfluidic channels in contrast to dip-type measurement in an open vessel.

Biochemical oxygen demand (BOD) is a key parameter for assessing water quality BOD is an indicator of the amount of biodegradable organic compounds and is the most widely used parameter for water quality monitoring. Therefore, it is used to ascertain the levels of organic waste present in water samples. BOD determination is an empirical test in which standardized laboratory procedures are used to determine the relative oxygen requirements of wastewater or effluents. The main disadvantage of $BOD_5$ measurement is that it requires 5 days for determination of BOD by observing the depletion of dissolved oxygen in that period. Therefore, a conventional BOD measurement allows only a subsequent evaluation of wastewater and is unsuitable for process control.

EXAMPLE 2

Disposable BOD Microsensor

Sensor Design—As in Example 1, Cyclic Olefin Copolymer (COC) was used as the sensor substrate as well as the material to create the microfluidic layer. It is a rugged, transparent polymer with inertness towards chemicals like acetone, unlike many other plastic materials. Use of the cost-effective COC and batch fabrication techniques allow these sensors to be disposable.

Figure 21:
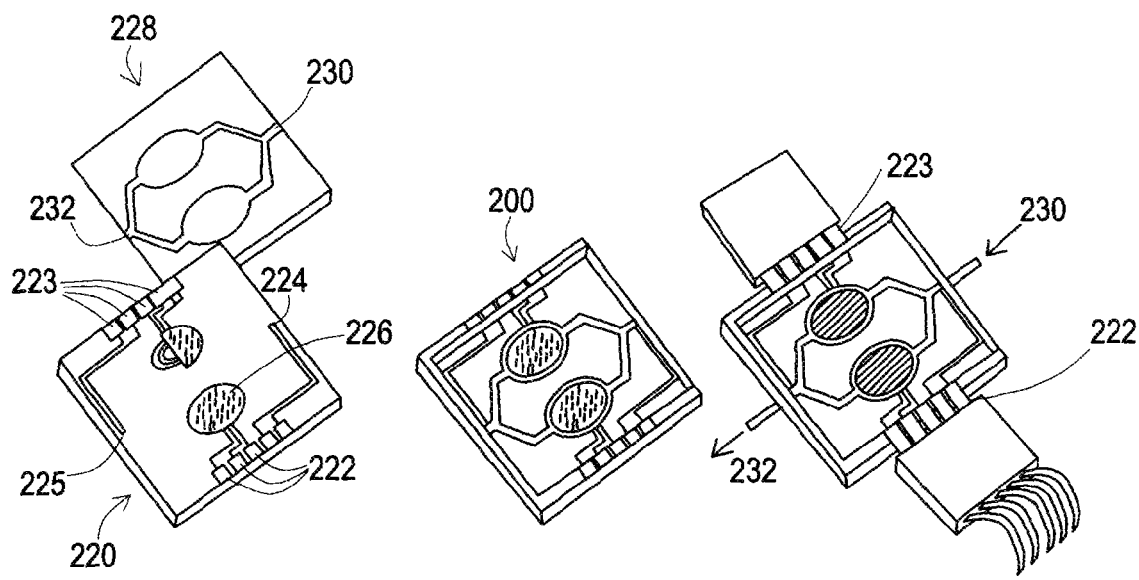
FIG. 21 is an exploded view of a Biochemical Oxygen Demand (BOD) sensor.

The BOD sensor 200 consists of 3 layers stacked one above the other as shown in FIG. 21. A bottom electrode layer 220 comprising 2 sets of sensor electrodes 222, 223 and one set of temperature sensors 224, 225 are covered with dissolved oxygen selective membrane (not shown). An intermediate microbial layer 226 of yeast *T. Cutaneum* immobilized on one set of sensor electrodes 222. Microbial stains and sensor structure are very important in the design. Some examples of well-known microbial strains are *Rhodococus Erythropolis*, *Issatchenkia Orientalis* and *Trichosporon Cutaneum*, the culture chosen for illustration of the present invention. An injection molded top microfluidic layer 228 with outlets 230, 232 for flow-through sample injection.

Figure 22:
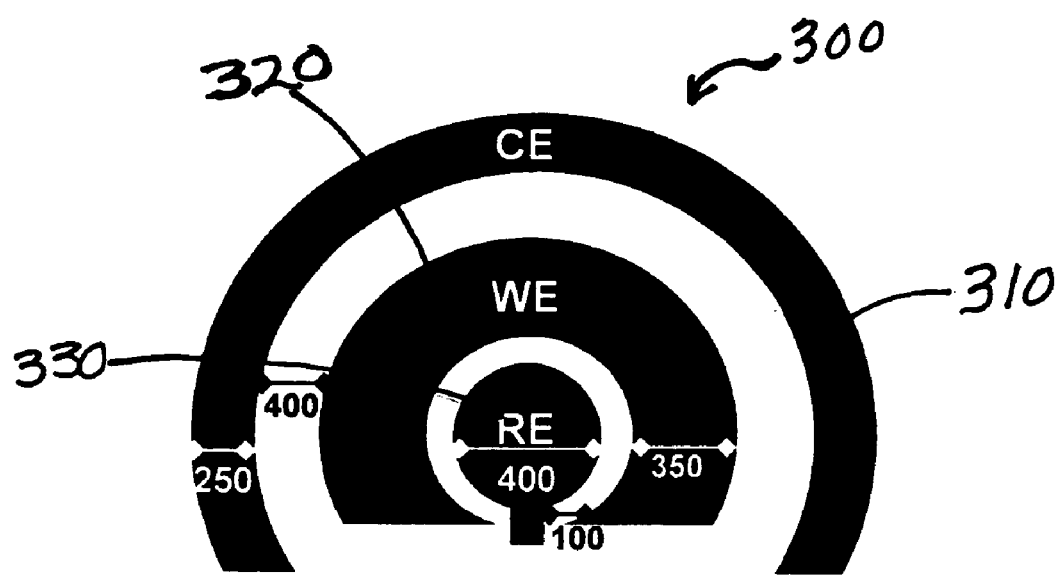
FIG. 22 is the upper half of working electrode (WE), reference electrode (RE) and counter electrode (CE) with dimensions in microns.

FIG. 22 shows the partial electrode structure of the BOD sensor. A ring type 3-electrode configuration 300 was chosen for amperometric sensing of dissolved oxygen. The 3-terminal design allows for faster response time as well as greater linearity. If linearity is maintained, the sensor signal can be directionally interpreted based on chemical concentration over the wide range. A counter electrode (CE) 310 measuring approximately 250 micrometers (mm) wide is spaced approximately 400 mm from a working electrode (WE) 320 that is approximately 350 mm wide; both strips are made with gold (Au). Spaced 100 mm inside the working electrode (WE) is a circular reference electrode (RE) 330 that is 400 mm in diameter. Silver/silver chloride (Ag/AgCl) on top of gold was used for the reference electrode (RE) 330. The counter (CE) 310, working (WE) 320 and reference (RE) electrode 330 are fabricated using photolithography, electroplating and chlorination.

Figure 23:
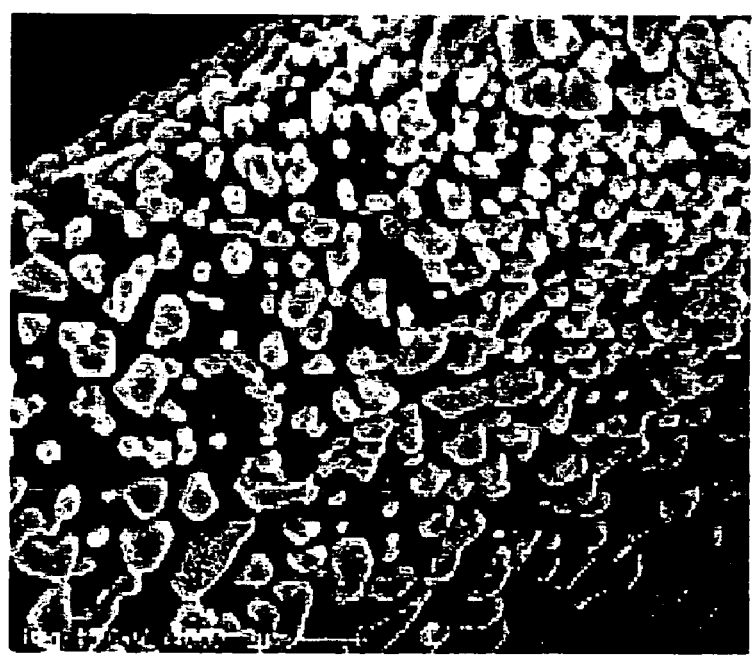
FIG. 23 is a Scanning Electron Microscope (SEM) image of immobilized yeast, *Trichosporon Cutaneum*.

A solid electrolyte containing KCl was screen printed on the sensor electrodes and silicone was spin coated as an oxygen permeable membrane. Yeast *T. Cutaneum*, shown in FIG. 23 was cultured in a yeast malt (YM) broth medium and aseptically transferred on top of one of the sensor electrodes. FIG. 23 is a scanning electron micrograph image of yeast *T. Cutaneum* at a magnification of 2 micrometers. Agarose gel was used to immobilize the microbial layer. This ensured a fixed amount of microorganisms with functional metabolic activities for the sensor lifetime.

Figure 24:
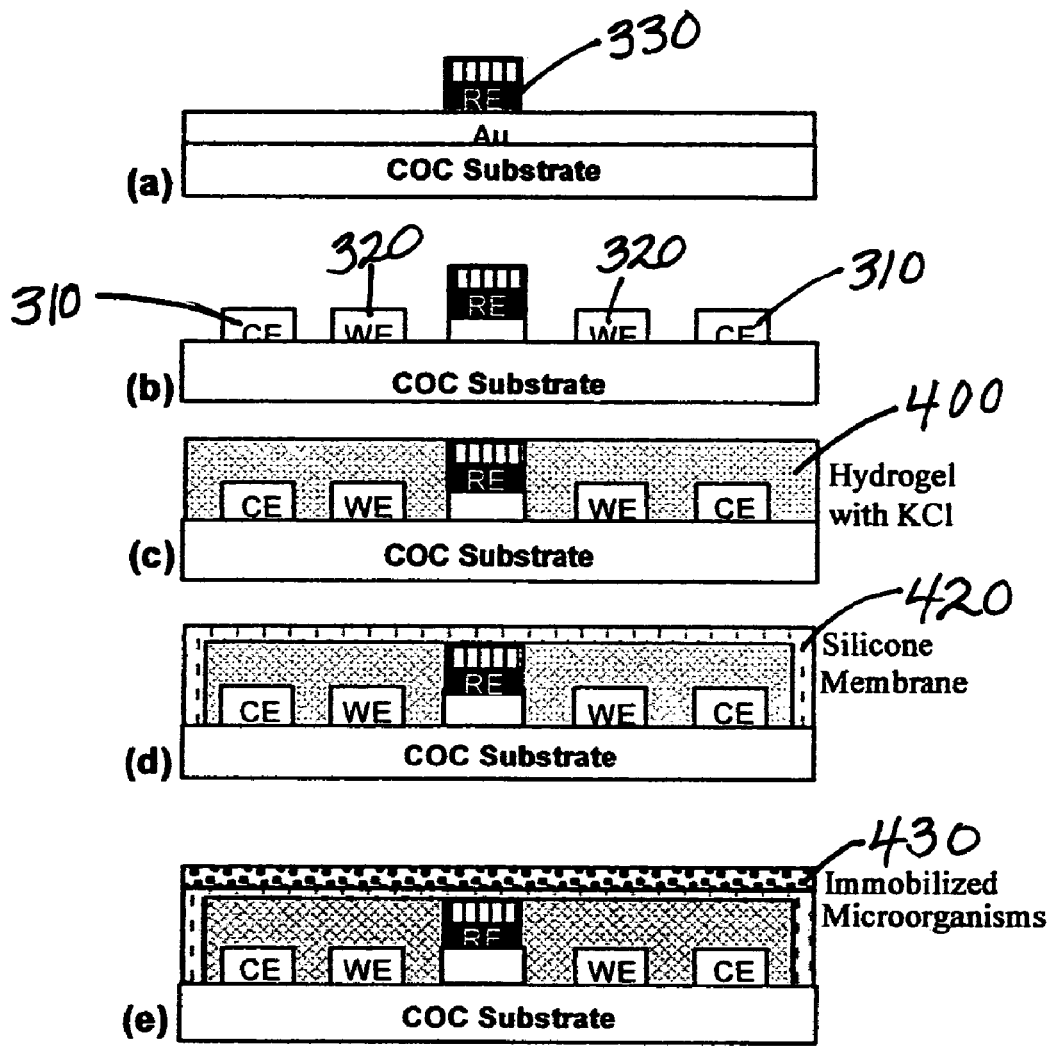
FIG. 24 shows the fabrication steps for the electrode layer and immobilized microorganism layer.

Referring now to FIG. 24, the fabrication steps for the bottom electrode layer and intermediate layer with immobilized microorganisms is illustrated. Step (a) is the formation of the Ag/AgCl reference electrode (RE) 330 on the cyclic olefin copolymer (COC) substrate. Step (b) is the patterning of the working electrode (WE) 320 and counter electrode (CE) 310. Step (c) is screen printing of solid electrolyte with potassium chloride (KCl) 400. Step (d) is the spin coating of silicone to form an oxygen permeable membrane 420. Step (e) is the immobilizing of microorganisms of intermediate microbial layer 226 (shown in FIG. 21) with Agarose gel 430.

Figure 25A:
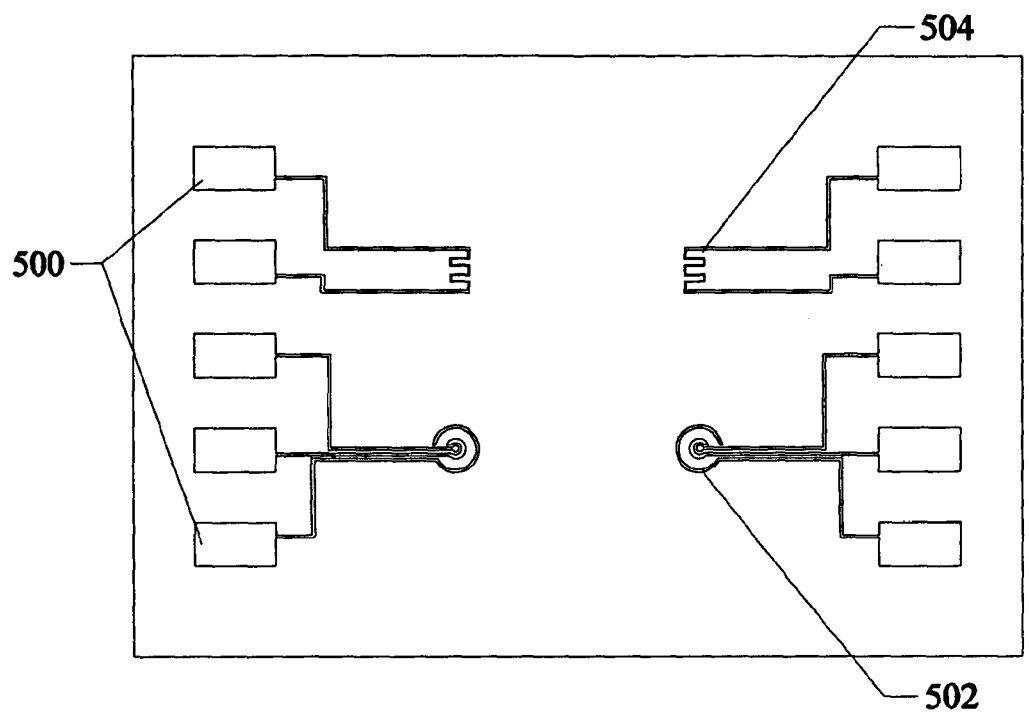
FIG. 25a is the fabricated BOD sensor layer.
Figure 25B:
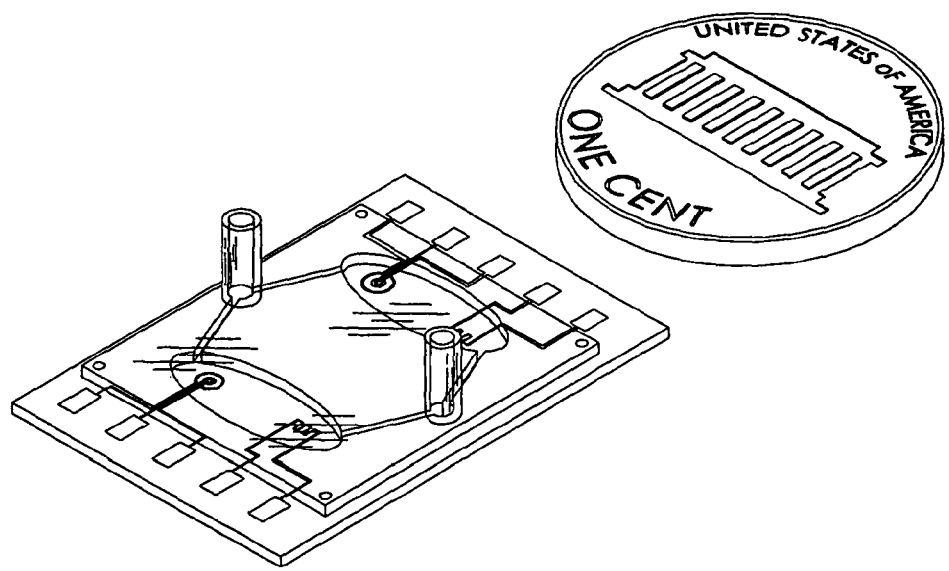
FIG. 25b is the assembled BOD sensor of the present invention.

The final BOD microsensor is obtained by adhesively packaging the bottom electrode layer 105 (shown in FIG. 11) with an intermediate microbial layer 226 (shown in FIG. 21) with the top fluidic layer 228 (shown in FIG. 21). The packaging of layers in the microsensor can also be accomplished by thermal bonding or any other means known to a person skilled in the art that does not interfere with the functioning of the sensor. FIG. 25*a* shows the electrode layer with contact pads 500, dissolved oxygen sensor 502 and temperature sensor 504. FIG. 25*b* is a photograph of the final assembled BOD sensor device which is approximately the size of a one-cent piece or penny in U.S. currency. The photograph clearly shows how this BOD microsensor can be both portable and disposable.

Testing and Results.

Figure 26:
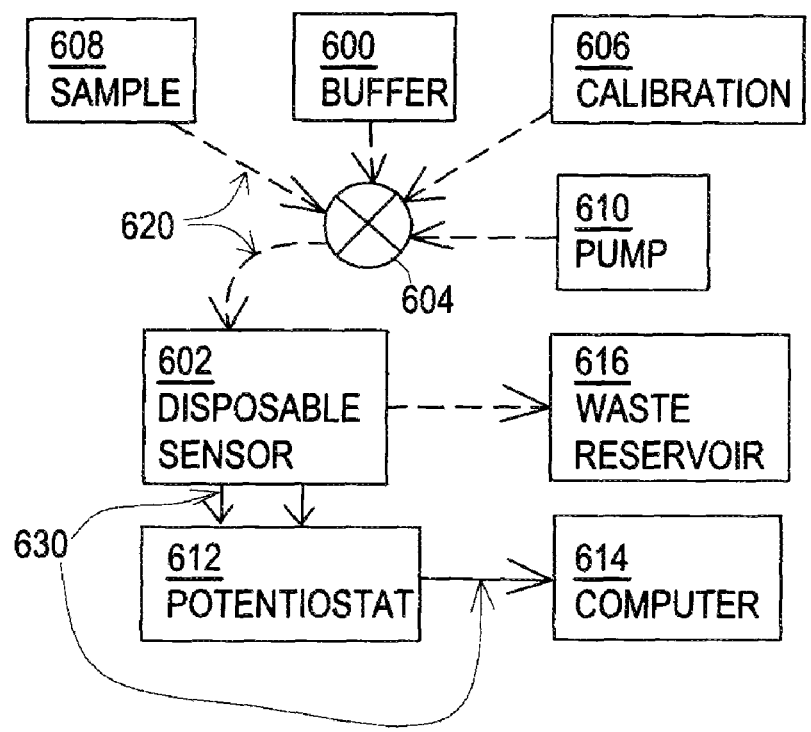
FIG. 26 is a flow diagram of the operational set up to test the BOD sensor with wastewater.

A 0.1 molar (M) phosphate buffer solution (PBS) was used to conduct the cyclic polarization and determine the working potential of the microsensor. Subsequently standard BOD solutions ranging from approximately 2 parts per million (ppm) to approximately 200 ppm were used to calibrate the sensor. Wastewater samples obtained from Eastern Wastewater Reclamation Facility (EWRF), Orlando, Fla., USA, were tested using the sensor. An external syringe pump was connected to the inlet on the microfluidic layer for flow-through sample injection. Inlet and outlets could connect to the standard 1/32" and 1/16" tubing respectively. 0.1 M PBS was used as a neutral run between testing the BOD solutions of varying concentrations. An external potentiostat was used to control the sensor operation. FIG. 26 is a flow diagram of the test setup.

In FIG. 26, a buffering agent 600 to conduct the cyclic polarization and determine the electrode working potential is introduced to a sensor 602 through valve 604. Standard BOD solutions are then used to calibrate 606 the sensors prior to injecting a sample 608, such as wastewater or drinking water. A pump 610 is connected to valve 604, to control fluid flow, to the sensor 602 which has an inlet port on the microfluidic layer for flow-through sample injection. The pump 610 is activated and the sample flows through the disposable sensor 602 comprising a top microfluidic layer adhesively stacked over a bottom electrode layer. The sensing circuitry in the electrode layer is connected to a power source, such as a battery. The current output signal is measured by the potentiostat 612 which reads the current flowing between working and counter electrodes. The current output data is displayed by a computer monitor 614 or hand-held display device.

Meanwhile, the fluid, sample is analyzed as it flows over the electrode layer and continues through the microfluidic layer to an outlet port and into a waste reservoir 616. As shown in FIG. 26, there is a distinct fluidic path 620 and an electrical path 630 connected by the disposable sensor 602. Sensor 602 can be replaced with a new, uncontaminated sensor unit as desired.

Cyclic polarization for the 0.1 M phosphate buffer solution (PBS) solution was conducted between −1 voltage (V) to +1 voltage (V) with respect to the reference electrode (RE) to characterize the sensor. The characterization led the selection of an operating potential of 300 mV for the sensor. At this operating potential, dissolved oxygen was reduced and flow of current was observed between the working electrode (WE) and the counter electrode (CE). Dissolved oxygen concentration was therefore indirectly indicated in the corresponding flow of current output signal. Part of the dissolved oxygen was utilized by the immobilized microbial matrix on one set of sensor electrodes, while the other sensor electrode which was left bare had differing dissolved oxygen concentration. This differential current was used as an indication of BOD.

The sensor was tested using standard BOD solutions and actual wastewater samples collected from Eastern Wastewater Reclamation Facility (EWRF), Orlando, Fla., USA. BOD values of approximately 3 ppm and approximately 193 ppm were measured for the actual wastewater samples (raw water and effluent) using the flow-through microbial sensor. Table 1 below shows the chemical BOD values calculated for various samples using the standard 5-day incubation procedure in APHA, AWWA, and WEF, "Standard Methods for the Examination of Water and Wastewater, American Public Health Association, Washington D.C., 19$^{th}$ Edition, (1995).

TABLE 1

5-Day BOD Calculations

| BOD Solution (ppm) | $BOD_5$ (mg/L) |
|---|---|
| 50 | 46 |
| 100 | 96 |
| 200 | 185 |
| Raw Water | 182 |
| Effluent | 2 |

Figure 27:
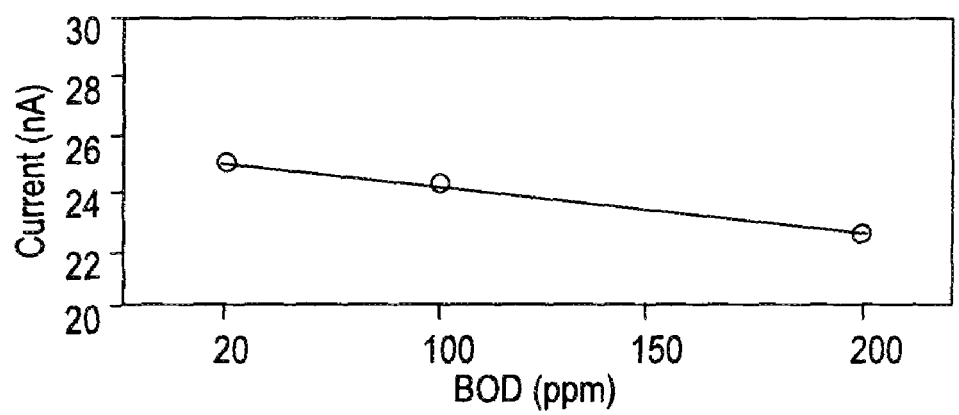
FIG. 27 is a plot of sensor output as a function of standard BOD measurement after incubating a sample at 20° C. for 5 days.

These values are in good agreement with the BOD values measured by the microbial sensor for various test samples. The sensor signals from various solutions were obtained electrochemically and compared with the chemically determined $BOD_5$ values; the comparison is shown in FIG. 27. The current is measured in nanoamperes (nA). Close correlation was observed between the chemical BOD and the sensor output signal obtained from the microsensor. The sensor showed a linear response with an average response time within one hour.

Thus, Example 2 demonstrates the development of a novel polymer based, disposable, flow-through microbial sensor. It is used to measure differential dissolved oxygen concentrations from two sets of electrodes to acquire a measure of BOD in water samples obtained from a wastewater reclamation process.

The advantages of the BOD microsensor of the present invention include, but are not limited to, a portable water quality monitoring system, fast BOD measurement, disposability because of its low cost, chemically inert polymer substrate, flow-through sample injection scheme and possible integration of on-chip optics. Analysis time and labor costs can be saved by separating a main control unit and a disposable and replaceable cartridge type sensor unit in this biosensor device.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for fabricating a multilayer disposable microsensor comprising the steps of:
    (a) forming a one-piece microfluidic package with a first side and a second side in steps consisting of:
    a-i selecting a mold cavity with an inlet for injecting a chemically inert molten polymer;
    a-ii defining a micro pattern of microfluidic channels having at least one set of interconnecting ports, the set having an inlet port and an outlet port, the set including one male port and one female port on a first side of the mold cavity;
    a-iii defining a plurality of inlet/outlet ports on a second side of the mold cavity that is opposite to the first side, the second side having one of a microfluidic channel and a combination of a microfluidic channel and a fluid reservoir, the first side and the second side of the one-piece microfluidic mold cavity together solely providing a one-piece, integrally formed one-piece microfluidic package;
    a-iv injecting a molten polymer into the mold cavity;
    a-v allowing the mold to cool;
    a vi allowing the molten polymer to become a rigid substrate;
    (a-vii) removing the rigid substrate with a plurality of inlet/outlet ports on the first side and a microfluidic channel and a combination of a microfluidic channel and a fluid reservoir on the second side thereby providing a one-piece, integrally formed, microfluidic package capable of permitting flow-through of a sample fluid;
    (b) preparing an electrode layer on a chemically inert, rigid polymer substrate that comprises a first set of electrodes, a second set of electrodes and one set of temperature sensors;
    I covering the electrode layer with a dissolved oxygen selective membrane;
    (d) preparing a microbial layer that is immobilized on one set of sensor electrodes;
    (e) sandwiching the microbial layer between the electrode layer and the microfluidic layer;
    (f) using an adhesive material to hold the electrode layer, the microbial layer and the microfluidic layer in a secure, stacked unitary arrangement; and
    (g) forming a multilayer, disposable microsensor wherein the top layer is the electrode layer with a first set of electrodes, a second set of electrodes and one set of temperature sensors, the middle layer is a microbial layer immobilized on one set of sensor electrodes and the bottom layer is the one-piece, integrally formed, microfluidic package capable of permitting flow-through of the sample fluid.

2. The method of claim 1 wherein the microfluidic channel is connected to a fluid reservoir.

3. The method of claim 1 wherein the chemically inert molten polymer of the microfluidic layer is a cyclic olefin copolymer.

4. The method of claim 1 wherein the chemically inert rigid polymer of the electrode layer is a cyclic olefin copolymer.

5. The method of claim 1 wherein the dissolved oxygen selective membrane is silicone.

6. The method of claim 1, wherein the sample fluid is selected from at least one of drinking water and waste water.

7. The method of claim 6, wherein the sample fluid is drinking water.

* * * * *